US011155809B2

(12) United States Patent
Lebofsky

(10) Patent No.: US 11,155,809 B2
(45) Date of Patent: Oct. 26, 2021

(54) DIGITAL PCR BARCODING

(71) Applicant: Bio-Rad Laboratories, Inc., Hercules, CA (US)

(72) Inventor: Ronald Lebofsky, Kensington, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 24 days.

(21) Appl. No.: 14/749,472

(22) Filed: Jun. 24, 2015

(65) Prior Publication Data

US 2016/0060621 A1    Mar. 3, 2016

Related U.S. Application Data

(60) Provisional application No. 62/016,568, filed on Jun. 24, 2014.

(51) Int. Cl.
*C12N 15/10* (2006.01)
*C12Q 1/6853* (2018.01)

(52) U.S. Cl.
CPC ....... *C12N 15/1065* (2013.01); *C12Q 1/6853* (2013.01)

(58) Field of Classification Search
CPC . C12N 15/1065; C12Q 1/6853; C12Q 1/6806
See application file for complete search history.

(56) References Cited

U.S. PATENT DOCUMENTS

| | | | |
|---|---|---|---|
| 4,438,258 A | 3/1984 | Graham | |
| 4,683,195 A | 7/1987 | Mullis et al. | |
| 4,683,202 A | 7/1987 | Mullis | |
| 5,695,934 A | 12/1997 | Brenner | |
| 5,714,330 A | 2/1998 | Brenner et al. | |
| 5,750,341 A | 5/1998 | Macevicz | |
| 5,900,481 A * | 5/1999 | Lough | C07F 9/2408 502/233 |
| 5,912,148 A | 6/1999 | Eggerding | |
| 6,130,073 A | 10/2000 | Eggerding | |
| 6,210,891 B1 | 4/2001 | Nyren et al. | |
| 6,258,568 B1 | 7/2001 | Nyren | |
| 6,306,597 B1 | 10/2001 | Macevicz | |
| 6,432,360 B1 | 8/2002 | Church | |
| 6,485,944 B1 | 11/2002 | Church et al. | |
| 6,511,803 B1 | 1/2003 | Church et al. | |
| 6,534,083 B2 | 3/2003 | Gilding et al. | |
| 6,787,308 B2 | 9/2004 | Balasubramanian et al. | |
| 6,818,395 B1 | 11/2004 | Quake et al. | |
| 6,833,246 B2 | 12/2004 | Balasubramanian | |
| 6,911,345 B2 | 6/2005 | Quake et al. | |
| 6,969,488 B2 | 11/2005 | Bridgham et al. | |
| 7,115,400 B1 | 10/2006 | Adessi et al. | |
| 7,169,560 B2 | 1/2007 | Lapidus et al. | |
| 7,170,050 B2 | 1/2007 | Turner et al. | |
| 7,282,337 B1 | 10/2007 | Harris | |
| 7,302,146 B2 | 11/2007 | Turner et al. | |
| 7,313,308 B2 | 12/2007 | Turner et al. | |
| 7,315,019 B2 | 1/2008 | Turner et al. | |
| 7,329,492 B2 | 2/2008 | Hardin et al. | |
| 7,405,281 B2 | 7/2008 | Xu et al. | |
| 7,476,503 B2 | 1/2009 | Turner et al. | |
| 7,482,120 B2 | 1/2009 | Buzby | |
| 7,501,245 B2 | 3/2009 | Quake et al. | |
| 7,668,697 B2 | 2/2010 | Volkov et al. | |
| 8,008,476 B2 | 8/2011 | Moya et al. | |
| 8,329,763 B2 | 12/2012 | Werner | |
| 9,029,085 B2 | 5/2015 | Agresti et al. | |
| 2002/0009591 A1 | 1/2002 | Gilding et al. | |
| 2003/0124564 A1* | 7/2003 | Trau | C08G 77/06 435/6.12 |
| 2005/0130173 A1 | 6/2005 | Leamon et al. | |
| 2007/0031857 A1 | 2/2007 | Makarov et al. | |
| 2007/0036511 A1 | 2/2007 | Lundquist et al. | |
| 2007/0072196 A1 | 3/2007 | Xu et al. | |
| 2007/0077564 A1 | 4/2007 | Roitman et al. | |
| 2007/0128133 A1 | 6/2007 | Eid et al. | |
| 2007/0134128 A1 | 6/2007 | Korlach | |
| 2007/0141598 A1 | 6/2007 | Turner et al. | |
| 2007/0161017 A1 | 7/2007 | Eid et al. | |
| 2007/0188750 A1 | 8/2007 | Lundquist et al. | |
| 2007/0196846 A1 | 8/2007 | Hanzel et al. | |
| 2007/0206187 A1 | 9/2007 | Lundquist et al. | |
| 2007/0231804 A1 | 10/2007 | Korlach et al. | |
| 2007/0238679 A1 | 10/2007 | Rank et al. | |
| 2008/0009007 A1 | 1/2008 | Lyle et al. | |
| 2008/0030628 A1 | 2/2008 | Lundquist et al. | |
| 2008/0032301 A1 | 2/2008 | Rank et al. | |
| 2008/0050747 A1 | 2/2008 | Korlach et al. | |

(Continued)

FOREIGN PATENT DOCUMENTS

CN    102719528 A    10/2012
WO    1997/030092 A2    8/1997

(Continued)

OTHER PUBLICATIONS

Claeboe et al.( Nucleic acids research 31.19 (2003): 5685-5691).*
Adessi et al., "Solid phase DNA amplification: characterisation of primer attachment and amplification mechanisms" *Nucleic Acid Res.*, 28 (20):E87 (2000), 8 pages.
Astier et al., "Toward single molecule DNA sequencing: direct identification of ribonucleoside and deoxyribonucleoside 5'-monophosphates by using an engineered protein nanopore equipped with a molecular adapter", *J. Am. Chem. Soc.*, 128(5)1705-1710 (2006).
Brenner et al., "Gene expression analysis by massively parallel signature sequencing (MPSS) on microbead arrays", *Nat. Biotechnol*, 18:630-634 (2000).

(Continued)

*Primary Examiner* — Sahana S Kaup

(74) *Attorney, Agent, or Firm* — Kilpatrick Townsend and Stockton LLP

(57) ABSTRACT

Methods, compositions, and kits are provided for nucleic acid analysis, including single cell analysis.

18 Claims, 12 Drawing Sheets

Specification includes a Sequence Listing.

(56) References Cited

U.S. PATENT DOCUMENTS

| | | |
|---|---|---|
| 2008/0080059 A1 | 4/2008 | Dixon et al. |
| 2008/0095488 A1 | 4/2008 | Foquet et al. |
| 2008/0108082 A1 | 5/2008 | Rank et al. |
| 2008/0128627 A1 | 6/2008 | Lundquist et al. |
| 2008/0145278 A1 | 6/2008 | Korlach |
| 2008/0152280 A1 | 6/2008 | Lundquist et al. |
| 2008/0152281 A1 | 6/2008 | Lundquist et al. |
| 2008/0153095 A1 | 6/2008 | Williams et al. |
| 2008/0153100 A1 | 6/2008 | Rank et al. |
| 2008/0157005 A1 | 7/2008 | Lundquist et al. |
| 2008/0160531 A1 | 7/2008 | Korlach |
| 2008/0165346 A1 | 7/2008 | Lundquist et al. |
| 2008/0176241 A1 | 7/2008 | Eid et al. |
| 2008/0176316 A1 | 7/2008 | Eid et al. |
| 2008/0176769 A1 | 7/2008 | Rank et al. |
| 2008/0199874 A1 | 8/2008 | Otto et al. |
| 2008/0199932 A1 | 8/2008 | Hanzel et al. |
| 2008/0206764 A1 | 8/2008 | Williams et al. |
| 2008/0212960 A1 | 9/2008 | Lundquist et al. |
| 2008/0241951 A1 | 10/2008 | Battulga et al. |
| 2009/0026082 A1 | 1/2009 | Rothberg et al. |
| 2009/0035777 A1 | 2/2009 | Kokoris et al. |
| 2009/0127589 A1 | 5/2009 | Rothberg et al. |
| 2010/0041561 A1* | 2/2010 | Gormley ............ C12Q 1/6855 506/2 |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0285975 A1* | 11/2010 | Mathies ............... B01F 3/0807 506/7 |
| 2010/0301398 A1 | 12/2010 | Rothberg et al. |
| 2011/0008775 A1 | 1/2011 | Gao et al. |
| 2011/0028334 A1* | 2/2011 | Hayden ............. C12Q 1/686 506/8 |
| 2011/0218123 A1 | 9/2011 | Weitz et al. |
| 2012/0108469 A1 | 5/2012 | Engelhardt et al. |
| 2012/0220494 A1* | 8/2012 | Samuels ........... C12N 15/1075 506/16 |
| 2013/0022569 A1 | 1/2013 | Uhrich et al. |
| 2013/0034592 A1 | 2/2013 | Yamamoto et al. |
| 2013/0274117 A1* | 10/2013 | Church ............... C12Q 1/6869 506/4 |
| 2013/0303407 A1* | 11/2013 | Makarov ............. C12P 19/34 506/26 |
| 2014/0155295 A1 | 6/2014 | Hindson et al. |
| 2014/0228255 A1* | 8/2014 | Hindson ............. C12Q 1/6876 506/26 |

FOREIGN PATENT DOCUMENTS

| | | | |
|---|---|---|---|
| WO | 2000/018957 A1 | 4/2000 | |
| WO | 2001/049240 A2 | 7/2001 | |
| WO | 2006/084132 A2 | 8/2006 | |
| WO | WO-2007140015 A2 * | 12/2007 | ........ B01L 3/502784 |
| WO | 2012/129363 A1 | 9/2012 | |
| WO | 2014/028537 A1 | 2/2014 | |
| WO | 2017/093676 A1 | 6/2014 | |
| WO | 2014/124338 A1 | 8/2014 | |
| WO | 2017/124336 A2 | 8/2014 | |
| WO | 2014/210353 A2 | 12/2014 | |
| WO | 2015/157567 A1 | 10/2015 | |
| WO | 2015/164212 A1 | 10/2015 | |
| WO | 2015/200869 A1 | 12/2015 | |
| WO | 2015/200871 A1 | 12/2015 | |
| WO | 2015/200891 A1 | 12/2015 | |
| WO | 2015/200893 A2 | 12/2015 | |
| WO | 2016/069939 A1 | 5/2016 | |
| WO | 2016/114970 A1 | 7/2016 | |
| WO | 2016/115273 A1 | 7/2016 | |
| WO | 2016/130578 A1 | 8/2016 | |
| WO | 2016/137973 A1 | 9/2016 | |
| WO | 2016/138148 A1 | 9/2016 | |
| WO | 2016/187179 A1 | 11/2016 | |
| WO | 2016/187256 A2 | 11/2016 | |
| WO | 2017/070056 A1 | 4/2017 | |
| WO | 2017/087910 A1 | 5/2017 | |
| WO | 2017/096158 A1 | 6/2017 | |
| WO | 2017/138984 A1 | 8/2017 | |
| WO | 2017/139690 A1 | 8/2017 | |

OTHER PUBLICATIONS

Clausell-Tormos et al., "Droplet-based microfluidic platforms for the encapsulation and screening of Mammalian cells and multicellular organisms", Chem Biol, 15(5):427-37 (2008).

Klein et al., "Droplet barcoding for single-cell transcriptomics applied to embryonic stem cells", Cell, 161(5):1187-201 (2015).

MacLean et al., "Application of 'next-generation' sequencing technologies to microbial genetics", Nature Rev. Microbiol., 7:287-296 (2009).

Macosko et al., "Highly Parallel Genome-wide Expression Profiling of Individual Cells Using Nanoliter Droplets", Cell, 161(5):1202-1214. (2015).

Margulies et al., "Genome Sequencing in Open Microfabricated High Density Picoliter Reactors", Nature, 437: 376-380 (2005).

Mitra et al., "Fluorescent in situ sequencing on polymerase colonies", Analytical Biochemistry, 320: 55-65 (2003).

Morozova et al., "Applications of next-generation sequencing technologies in functional genomics", Genomics, 92: 255-264 (2008).

Pennisi, "Semiconductor Inspire New Sequencing Technologies", Science, 327(5970): 1190 (2010).

Shendure et al., "Accurate Multiplex Polony Sequencing of an Evolved Bacterial Genome", Science, 309:1728-1732 (2005).

Shiroguchi et al., "Digital RNA sequencing minimizes sequence-dependent bias and amplification noise with optimized single-molecule barcodes", Proc Natl Acad Sci U S A., 109(4):1347-52 (2012).

Smith et al., "Highly-multiplexed barcode sequencing: an efficient method for parallel analysis of pooled samples", Nucleic Acids Research, 38(13): e142 11, (2010).

Van Balkom et al., "Quantitative and qualitative analysis of small RNAs in human endothelial cells and exosomes provides insights into localized RNA processing, degradation and sorting", J Extracell Vesicles, 4:26760 (2015), 14 pages.

Voelkerding et al., "Next-generation sequencing: From Basic Research to Diagnostics", Clinical Chem., 55: 641-658 (2009).

International Search Report and Written Opinion dated Dec. 4, 2015 issue for PCT/US15/37525, 15 pages.

Georgiou et al., "The Promise and Challenge of High-Throughput Sequencing of the Antibody Repertoire", Nature Biotechnology, vol. 32, No. 2, 1-11 (Feb. 2014).

Extended European Search Report from EP 15790435.0, dated Nov. 21, 2017, 15 pages.

Response to Extended European Search Report in EP Appln. 15790435.0 dated Jun. 15, 2018; 5 pages.

"NEBNext® Sample Preparation; Workflow Overviews & Products" Poster; Version 1; New England BioLabs, Inc.; Oct. 2014; 1 page.

Kumar, N.V. et al.; "Inefficient excision of uracil from loop regions of DNA oligomers by E.coli uracil DNA glycosylase"; Nucleic Acids Research; vol. 22, No. 18; 1994; pp. 3737-3741.

* cited by examiner

SEQUENCE LISTING

<160> NUMBER OF SEQ ID NOS: 29

<210> SEQ ID NO 1
<211> LENGTH: 10
<212> TYPE: DNA
<213> ORGANISM: Artificial Sequence

```
<220> FEATURE:
<223> OTHER INFORMATION: synthetic oligonucleotide
<220> FEATURE:
<221> NAME/KEY: misc_feature
<222> LOCATION: (1)..(10)
<223> OTHER INFORMATION: N is A, C, G or T

<400> SEQUENCE: 1 nnnnnngtaa                                                                 10

<210> SEQ ID NO 2
<211> LENGTH: 10
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(10)
<223> OTHER INFORMATION: N is A, C, G or T

<400> SEQUENCE: 2 nnnnnnacgc                                                                 10

<210> SEQ ID NO 3
<211> LENGTH: 10
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(10)
<223> OTHER INFORMATION: N is A, C, G or T

<400> SEQUENCE: 3 nnnnnncatg                                                                 10

<210> SEQ ID NO 4
<211> LENGTH: 10
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(10)
<223> OTHER INFORMATION: N is A, C, G or T

<400> SEQUENCE: 4 nnnnnntgct                                                                 10

<210> SEQ ID NO 5
<211> LENGTH: 14
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(14)
<223> OTHER INFORMATION: N is A, C, G or T

<400> SEQUENCE: 5
nnnnnntgct nnnn                                                            14

<210> SEQ ID NO 6
<211> LENGTH: 14
<212> TYPE: DNA
```

```
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(14)
<223> OTHER INFORMATION: N is A, C, G or T

<400> SEQUENCE: 6
nnnnnncatg nnnn                                                       14

<210> SEQ ID NO 7
<211> LENGTH: 14
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(14)
<223> OTHER INFORMATION: N is A, C, G or T

<400> SEQUENCE: 7
nnnnnnacgc nnnn                                                       14

<210> SEQ ID NO 8
<211> LENGTH: 14
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(14)
<223> OTHER INFORMATION: N is A, C, G or T

<400> SEQUENCE: 8
nnnnnngtaa nnnn                                                       14

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(20)
<223> OTHER INFORMATION: N is A, C, G or T

<400> SEQUENCE: 9
nnnnnntgct nnnnnnnnnn                                                 20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(20)
<223> OTHER INFORMATION: N is A, C, G or T

<400> SEQUENCE: 10
nnnnnncatg nnnnnnnnnn                                                 20

<210> SEQ ID NO 11
<211> LENGTH: 20
```

```
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(20)
<223> OTHER INFORMATION: N is A, C, G or T

<400> SEQUENCE: 11
nnnnnnacgc nnnnnnnnnn                                              20

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(20)
<223> OTHER INFORMATION: N is A, C, G or T

<400> SEQUENCE: 12
nnnnnngtaa nnnnnnnnnn                                              20

<210> SEQ ID NO 13
<211> LENGTH: 56
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: B is C, G, or T
<220> FEATURE:
<221> NAME/KEY: misc_feature
<222> LOCATION: (2)..(56)
<223> OTHER INFORMATION: N is A, C, G, or T

<400> SEQUENCE: 13
baaaaaaaaa aaaaaaaaaa aaaaannnnn nnnnnngcgt cctgacagga ggcttg      56

<210> SEQ ID NO 14
<211> LENGTH: 53
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(53)
<223> OTHER INFORMATION: N is A, C, G or T

<400> SEQUENCE: 14
gcgtcctgac aggaggcttg nnnnnnnnnn agatcggaag agcacacgtc tga         53

<210> SEQ ID NO 15
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 15
tcagacgtgt gctcttccga tct                                          23

<210> SEQ ID NO 16
```

```
<211> LENGTH: 88
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: B is C, G, or T
<220> FEATURE:
<221> NAME/KEY: misc_feature
<222> LOCATION: (2)..(88)
<223> OTHER INFORMATION: N is A, C, G or T

<400> SEQUENCE: 16
baaaaaaaaa aaaaaaaaaa aaaaannnnn nnnnngcgtc ctgacaggag gcttgnnnnn    60
nnnnnagatc ggaagagcac acgtctga                                       88

<210> SEQ ID NO 17
<211> LENGTH: 88
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(87)
<223> OTHER INFORMATION: N is A, C, G, or T
<220> FEATURE:
<221> NAME/KEY: misc_feature
<222> LOCATION: (88)..(88)
<223> OTHER INFORMATION: V is A, C, or G

<400> SEQUENCE: 17
tcagacgtgt gctcttccga tctnnnnnnn nnncaagcct cctgtcagga cgcnnnnnnn    60 nnntttttt tttttttttt tttttttv                                        88

<210> SEQ ID NO 18
<211> LENGTH: 25
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: B is C, G, or U (or T)

<400> SEQUENCE: 18
baaaaaaaaa aaaaaaaaaa aaaaa                                          25

<210> SEQ ID NO 19
<211> LENGTH: 79
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (79)..(79)
<223> OTHER INFORMATION: V is A, C, or G

<400> SEQUENCE: 19
aatgatacgg cgaccaccga gatctacact ctttccctac acgacgctct tccgatcttt    60
tttttttttt tttttttv                                                  79

<210> SEQ ID NO 20
<211> LENGTH: 24
```

```
<212> TYPE: DNA
<213> ORGANISM: Artificial Sequence
<220> FEATURE:
<223> OTHER INFORMATION: synthetic oligonucleotide - represents 5' end
      flanking an index barcode oligonucleotide sequence

<400> SEQUENCE: 20
caagcagaag acggcatacg agat                                            24

<210> SEQ ID NO 21
<211> LENGTH: 34
<212> TYPE: DNA
<213> ORGANISM: Artificial Sequence
<220> FEATURE:
<223> OTHER INFORMATION: synthetic oligonucleotide - represents 3' end
      flanking an index barcode oligonucleotide sequence

<400> SEQUENCE: 21
gtgactggag ttcagacgtg tgctcttccg atct                                 34

<210> SEQ ID NO 22
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 22
tctagccttc tcgcagcaca tccctttctc acatctagag ccaccagcgg catagtaa       58

<210> SEQ ID NO 23
<211> LENGTH: 202
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(202)
<223> OTHER INFORMATION: N is A, C, G, or T
<220> FEATURE:
<221> NAME/KEY: misc_feature
<222> LOCATION: (79)..(79)
<223> OTHER INFORMATION: V is A, C, or G
<220> FEATURE:
<221> NAME/KEY: misc_feature
<222> LOCATION: (79)..(79)
<223> OTHER INFORMATION: 3' end is flanked by cDNA sequence
      (sequence/length variable and unknown)
<220> FEATURE:
<221> NAME/KEY: misc_feature
<222> LOCATION: (80)..(80)
<223> OTHER INFORMATION: B is C, G, or T
<220> FEATURE:
<221> NAME/KEY: misc_feature
<222> LOCATION: (80)..(80)
<223> OTHER INFORMATION: 5' end is preceded by cDNA sequence
      (sequence/length variable and unknown)
<220> FEATURE:
<221> NAME/KEY: misc_feature
<222> LOCATION: (178)..(178)
<223> OTHER INFORMATION: 3' end is flanked by index barcode sequence
      (sequence/length variable and unknown)
<220> FEATURE:
<221> NAME/KEY: misc_feature
<222> LOCATION: (179)..(179)
<223> OTHER INFORMATION: 5' end is preceded by index barcode sequence
      (sequence/length variable and unknown)

<400> SEQUENCE: 23
aatgatacgg cgaccaccga gatctacact ctttccctac acgacgctct tccgatcttt     60
```

```
tttttttttt tttttttttvb aaaaaaaaaa aaaaaaaaaa aaaannnnnn nnnngcgtcc      120
tgacaggagg cttgnnnnnn nnnnagatcg gaagagcaca cgtctgaact ccagtcacat      180
ctcgtatgcc gtcttctgct tg                                              202
```

<210> SEQ ID NO 24
<211> LENGTH: 34
<212> TYPE: DNA
<213> ORGANISM: Artificial Sequence
<220> FEATURE:
<223> OTHER INFORMATION: synthetic oligonucleotide primer

<400> SEQUENCE: 24

```
gtgactggag ttcagacgtg tgctcttccg atct                                 34
```

<210> SEQ ID NO 25
<211> LENGTH: 202
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(202)
<223> OTHER INFORMATION: N is A, C, G, or T
<220> FEATURE:
<221> NAME/KEY: misc_feature
<222> LOCATION: (24)..(24)
<223> OTHER INFORMATION: 3' end is flanked by index barcode sequence
      (sequence/length variable and unknown)
<220> FEATURE:
<221> NAME/KEY: misc_feature
<222> LOCATION: (25)..(25)
<223> OTHER INFORMATION: 5' end is preceded by index barcode sequence
      (sequence/length variable and unknown)
<220> FEATURE:
<221> NAME/KEY: misc_feature
<222> LOCATION: (123)..(123)
<223> OTHER INFORMATION: 3' end is flanked by cDNA sequence
      (sequence/length variable and unknown)
<220> FEATURE:
<221> NAME/KEY: misc_feature
<222> LOCATION: (123)..(123)
<223> OTHER INFORMATION: V is A, C, and G
<220> FEATURE:
<221> NAME/KEY: misc_feature
<222> LOCATION: (124)..(124)
<223> OTHER INFORMATION: B is C, G, or T
<220> FEATURE:
<221> NAME/KEY: misc_feature
<222> LOCATION: (124)..(124)
<223> OTHER INFORMATION: 5' end is preceded by cDNA sequence
      (sequence/length variable and unknown)

<400> SEQUENCE: 25

```
caagcagaag acggcatacg agatgtgact ggagttcaga cgtgtgctct tccgatctnn      60
nnnnnnnnca agcctcctgt caggacgcnn nnnnnnnntt tttttttttt tttttttttt     120
ttvbaaaaaa aaaaaaaaaa aaaaagatcg gaagagcgtc gtgtagggaa agagtgtaga     180
tctcggtggt cgccgtatca tt                                              202
```

<210> SEQ ID NO 26
<211> LENGTH: 33
<212> TYPE: DNA
<213> ORGANISM: Artificial Sequence
<220> FEATURE:
<223> OTHER INFORMATION: synthetic oligonucleotide primer

<400> SEQUENCE: 26

```
acactctttc cctacacgac gctcttccga tct                                  33
```

```
<210> SEQ ID NO 27
<211> LENGTH: 32
<212> TYPE: DNA
<213> ORGANISM: Artificial Sequence
<220> FEATURE:
<223> OTHER INFORMATION: synthetic oligonucleotide primer

<400> SEQUENCE: 27
agatcggaag agcacacgtc tgaactccag tc                                32

<210> SEQ ID NO 28
<211> LENGTH: 29
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: 5' Hexachloro-fluorescein (HEX) labeled
<220> FEATURE:
<221> NAME/KEY: misc_feature
<222> LOCATION: (29)..(29)
<223> OTHER INFORMATION: 3' black hole quencher (BH3) labeled

<400> SEQUENCE: 28
aagagcgtcg tgtagggaaa gagtgtaga                                    29

<210> SEQ ID NO 29
<211> LENGTH: 26
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: 5' fluorescein (FAM) labeled
<220> FEATURE:
<221> NAME/KEY: misc_feature
<222> LOCATION: (26)..(26)
<223> OTHER INFORMATION: 3' black hole quencher (BHQ3) labeled

<400> SEQUENCE: 29
agagcacacg tctgaactcc agtcac                                       26
```

DIGITAL PCR BARCODING

CROSS-REFERENCES TO RELATED APPLICATIONS

This application claims priority to U.S. Provisional Application No. 62/016,568, filed Jun. 24, 2014, the contents of which are incorporated by reference in their entirety for all purposes.

BACKGROUND OF THE INVENTION

The individual cells of multicellular organisms often exhibit great diversity in gene expression and/or genotype, even among cells of the same tissue or cell-type. For example, during B-cell maturation, the cells undergo somatic recombination and hypermutation to generate a highly diverse antibody repertoire. As another example, tumor cells can develop genomic heterogeneity due to, e.g., dysregulation of checkpoint genes. Similarly, individual cells of a population of clonal unicellular organisms can present heterogeneous gene regulation or protein expression patterns, even when present in the same culture. Consequently, it is increasingly recognized that single-cell analysis can provide information that is obscured by traditional analytical approaches that analyze combined material from multiple cells. Moreover, application of single-genome analysis and/or gene expression analysis to a population of cells can reveal the natural diversity of gene expression and genotype when performed on a large number of cells. Such an approach can be useful, e.g., for analyzing the progression of cancer, understanding the development of autoimmune disorders, guiding the improvement of vaccines, and to gain a better understanding of natural biological processes. More generally, compositions, methods, kits, and/or systems for improved high throughput sequence analysis can be useful, e.g., for analyzing the progression of cancer, understanding the development of autoimmune disorders, guiding the improvement of vaccines, and to gain a better understanding of natural biological processes.

BRIEF SUMMARY OF THE INVENTION

Provided herein are methods, compositions, and kits for nucleic acid analysis. For example, methods, compositions, and kits described herein can be used for genome or gene expression analysis at the single cell level. In some embodiments, such methods, compositions, and kits allow for high-throughput and/or highly parallel analysis of individual cells by, e.g., gene expression, protein expression, and/or genome analysis.

In a first aspect, the present invention provides a partition containing a particle comprising a solid support surface, the solid support surface having a plurality of oligonucleotide primers conjugated thereon, wherein the plurality of oligonucleotide primers comprise: a 3' end that is available for ligation and/or extension by a polymerase; a 5' end that is linked to the solid support surface; and at least one barcode region. In some embodiments, the at least one barcode region comprises a partition-specific barcode, wherein the partition-specific barcode is substantially the same in the plurality of oligonucleotide primers conjugated to the solid support surface. In some embodiments, the at least one barcode region comprises a molecular barcode, wherein the molecular barcode of each of the plurality of oligonucleotides conjugated to the solid support surface is substantially unique.

In some embodiments, the at least one barcode region comprises a particle barcode and a molecular barcode. In some embodiments, the plurality of oligonucleotide primers comprise: a first defined region comprising a defined sequence of 10-100 nucleotides; a particle barcode comprising 6-20 nucleotides, wherein all, substantially all, or a majority of the plurality of oligonucleotide primers comprise the same particle barcode; and a molecular barcode comprising 6-20 nucleotides, wherein all, or substantially all, of the plurality of oligonucleotide primers comprise a unique molecular barcode. In some embodiments, the first defined sequence comprises a 3' capture region. In some embodiments, the capture region comprises a randomer, a poly-thymine, or a poly-adenosine sequence.

In some embodiments, the plurality of oligonucleotide primers conjugated to the solid support surface each comprise a hairpin region. In some embodiments, the hairpin region comprises a uracil. In some embodiments, the plurality of oligonucleotide primers each comprise a uracil at the 5' end of the oligonucleotide. In some embodiments, the plurality of oligonucleotide primers are conjugated to the solid support surface via a disulfide linkage. In some embodiments, the oligonucleotide primers comprise a double stranded region along at least a portion of the 3' end of the primers. In some embodiments, the plurality of oligonucleotide primers are double stranded. In some embodiments, the double stranded oligonucleotides or the portions of the oligonucleotides that are double stranded comprise a passivated 5' end. In some embodiments, the passivated 5' end comprises a 5' hydroxyl group (OH). In some embodiments, the partition comprises a droplet. In some embodiments, the partition can contain at least 10, 100; 200; 300; 500; 750; 1000; 2500; 5000; 7,500; 10,000; 15,000; 20,000; 30,000; 50,000; 100,000; $1\times10^6$; $1\times10^7$; or more copies of the partition-specific barcode, wherein the copies are identical or substantially identical, and unique or substantially unique as compared to partition-specific barcodes in other partitions, if present.

In a second aspect, the present invention provides a plurality of any one of the foregoing partitions, wherein the plurality of partitions comprises at least about 1,000; 10,000; 50,000; 100,000; 500,000; 1,000,000 or more particles comprising unique particle barcodes, wherein the unique particle barcodes are substantially the same for each particle and substantially unique between particles. In some embodiments, the partitions comprise, on average, 1 or fewer particles per partition. In some embodiments, the partitions comprise oligonucleotides cleaved from, on average, one or fewer barcoded particles. In some embodiments, the plurality of partitions comprise target nucleic acid. In some embodiments, the plurality of partitions comprise, on average, target nucleic acid of 1 or fewer cells per partition. In some embodiments, the target nucleic acid is mRNA and the particles comprise a poly-thymine capture region. In some embodiments, the target nucleic acid is cDNA and the particles comprise a poly-adenosine or poly-thymine capture region. In some embodiments, the partitions comprise droplets.

In a third aspect, the present invention provides a method of making any one of the foregoing partitions, the method comprising: sequentially conjugating a plurality of reverse amidite nucleotides to a solid support surface to generate a plurality of oligonucleotide primers linked to the solid support surface at the 5' end; and partitioning the solid support surface. In some embodiments, the conjugating comprises: (a) conjugating an equikinetic or equimolar mixture of reverse amidite nucleotides to the 3' end of the 5' linked oligonucleotide primers; and (b) repeating (a) from 6-20 times to thereby generate a plurality of unique molecular barcodes. In some embodiments, the conjugating comprises linking the 5' end of the oligonucleotide primers to the solid support surface via disulfide linkage. In some embodiments, the partitioning comprises partitioning the solid support surface into a droplet.

In a fourth aspect, the present invention provides a method of making any one of the foregoing plurality of partitions, the method comprising: (a) providing a plurality of particles comprising solid support surfaces; (b) conjugating a reverse amidite nucleotide to the solid support surfaces of the plurality of particles, wherein the conjugating is performed in at least four separate reactions, each reaction conjugating a different nucleotide, wherein after the conjugating, the particles are combined and mixed; (c) repeating (a) from 6-20 times, thereby generating a plurality of barcoded particles, wherein the individual barcoded particles comprise a plurality of copies of an oligonucleotide barcode unique to the particle, wherein the unique particle barcodes are substantially the same for each particle and substantially unique between particles; and (d) partitioning the plurality of barcoded particles. In some embodiments, the method further comprises, prior to the step of partitioning: conjugating a nucleotide mixture to the plurality of barcoded particles; and repeating (a) from 6-20 times, thereby generating a plurality of particles comprising particle barcodes and molecular barcodes. In some embodiments, the partitioning comprises partitioning the plurality of barcoded particles into a plurality of droplets.

In a fifth aspect, the present invention provides a method of analyzing the nucleic acid of a plurality of cells comprising: providing a plurality of any one of the foregoing partitions (e.g., droplets), wherein each partition comprises: a particle comprising a population of oligonucleotides having a barcode unique for that particle and a capture sequence; and a sample comprising a target nucleic acid; optionally cleaving the oligonucleotide primers conjugated to the plurality of particles from the particles; hybridizing the capture sequence, or a portion thereof, of the oligonucleotide primers to at least a portion of the target nucleic acid in each partition; performing template directed nucleic acid polymerization of the hybridized oligonucleotide primers, thereby covalently attaching the oligonucleotide primers to at least a portion of the target nucleic acid in each partition, wherein the template directed nucleic acid polymerization is performed before or after combining partitions; combining the partitions; and performing high throughput sequencing.

In some embodiments, the method comprises combining partitions and then performing template directed nucleic acid polymerization of the hybridized oligonucleotide primers. In some embodiments, the method comprises performing template directed nucleic acid polymerization of the hybridized oligonucleotide primers, and then combining the partitions. In some embodiments, the sample comprising target nucleic acid comprises a cell containing the target nucleic acid. In some embodiments, prior to the hybridizing, the cell is lysed.

In a sixth embodiments, the present invention provides a method of analyzing the nucleic acid of a plurality of cells comprising: providing any one of the foregoing plurality of partitions, wherein each partition comprises: a particle comprising a population of oligonucleotides having a barcode unique for that particle and a capture sequence; and a sample comprising a target nucleic acid; optionally cleaving the oligonucleotide primers conjugated to the plurality of particles from the particles; ligating the oligonucleotide primers to at least a portion of the target nucleic acid in each partition, thereby covalently attaching the oligonucleotide primers to at least a portion of the target nucleic acid in each partition, wherein the ligating is performed before combining partitions; combining the partitions; and performing high throughput sequencing.

In some embodiments, the sample comprising target nucleic acid comprises a cell containing the target nucleic acid. In some embodiments, prior to the ligating, the cell is lysed. In some embodiments, the sample comprising target nucleic acid comprises DNA. In some embodiments, the sample comprising target nucleic acid comprises long fragment DNA. In some embodiments, the DNA is double stranded.

In another aspect, the present invention provides a dual barcoded particle comprising a solid support surface, the solid support surface having a plurality of oligonucleotide primers conjugated thereon, wherein the plurality of oligonucleotide primers comprise: a first defined region comprising a defined sequence of 10-100 nucleotides; a particle barcode comprising 6-20 nucleotides, wherein all, substantially all, or a majority of the plurality of oligonucleotide primers comprise the same particle barcode; and a molecular barcode comprising 6-20 nucleotides, wherein all, or substantially all, of the plurality of oligonucleotide primers comprise a unique molecular barcode.

In some embodiments, the particle further comprises a second defined region comprising a defined sequence of 10-100 nucleotides. In some cases, the first defined sequence comprises a capture sequence for capturing nucleic acid. In some cases, the second defined sequence comprises a primer binding site, or the complement thereof. In some cases, the capture sequence comprises 10-25, 15-30, or 20-45 thymine nucleotides, or more. In some cases, the first defined region comprises one or more uracil nucleotides. In some cases, the particle comprises, from 3' to 5' the first defined sequence, the particle barcode, and the molecular barcode. In other cases, the particle comprises, from 5' to 3' the first defined sequence, the particle barcode, and the molecular barcode. In some cases, the second defined sequence is 5' of the molecular barcode. In some cases, the second defined sequence is 3' of the molecular barcode.

In another aspect, the present invention provides a plurality of any of the foregoing dual barcoded particles, wherein the plurality of particles comprises at least about 1,000; 10,000; 50,000; 100,000; 500,000; 1,000,000 or more unique particle barcodes. In some cases, the plurality of dual barcoded particles comprises at least 1,000; 10,000; 50,000; 100,000; 500,000; 1,000,000 or more particles.

In another aspect, the present invention provides a kit comprising any one of the foregoing plurality of dual barcoded particles and further comprising reagents for partitioning the plurality of particles in a plurality of partitions. In some embodiments, the reagents for partitioning the plurality of particles in a plurality of partitions comprise a water immiscible liquid. In some embodiments, the reagents for partitioning the plurality of particles in a plurality of partitions comprise an apparatus comprising a plurality of microchannels, or a plurality of micro- or nano-wells.

In another aspect, the present invention provides a method of generating a plurality of barcoded particles from a plurality of precursor particles, the method comprising: (a). conjugating a nucleotide to the plurality of precursor particles, wherein the conjugating is performed in at least four separate reactions, each reaction conjugating a different nucleic acid, wherein after the conjugating, the particles are combined and mixed; (b). repeating (a) from 6-20 times, thereby generating a plurality of barcoded particles, wherein the individual barcoded particles comprise a plurality of identical or substantially identical copies of an oligonucleotide barcode unique to the particle.

In some embodiments, the method further comprises: conjugating a nucleotide mixture to the oligonucleotides (e.g., 5' or 3' oligonucleotide ends) of a plurality of barcoded particles; and repeating (a) from 6-20 times, thereby generating a plurality of particles comprising particle barcodes and molecular barcodes. In some embodiments, the method further comprises conjugating a defined sequence to the plurality of barcoded particles, wherein the defined sequence comprises a capture sequence for capturing nucleic acid. In some embodiments, the defined sequence comprises one or more uracil nucleotides. In some cases, the defined sequence comprising the capture sequence is conjugated to the particles before the particle barcodes are generated. In some cases, the method further comprises conjugating a second defined sequence to the plurality of barcoded particles, wherein the second defined sequence comprises a primer binding site. In some cases, the second defined sequence is conjugated to the particles after the molecular barcodes are generated.

In another aspect, the present invention provides a method of analyzing the nucleic acid of a plurality of cells comprising: providing a plurality of barcoded particles, wherein each particle comprises a population of oligonucleotides having a barcode unique for that particle and a capture sequence; providing a population of cells; partitioning the plurality of particles and the population of cells, thereby generating a plurality of partitions having a single particle and nucleic acid from a single cell, in each partition; lysing the population of cells in the partitions; optionally cleaving the oligonucleotide primers conjugated to the plurality of particles from the particles; hybridizing the capture sequence, or a portion thereof, to at least a portion of the nucleic acid of the single cell in each partition; performing template directed nucleic acid polymerization, thereby covalently attaching the oligonucleotide primers to at least a portion of the nucleic acid of the single cell in each partition; combining the partitions; and performing high throughput sequencing. In some cases, the cleaving is performed prior to lysing the cells. In some cases, the cleaving is performed after lysing the cells. In some cases, the cleaving is performed simultaneously with the lysing of the cells.

In some embodiments, the partitioning comprises: partitioning the plurality of barcoded particles to generate a plurality of partitions having a single barcoded particle; after partitioning the plurality of particles, cleaving the oligonucleotides from the barcoded particles and partitioning the population of cells into the plurality of partitions having a single barcoded particle, thereby generating a plurality of partitions having a single cell and a population of oligonucleotides from a single barcoded particle. In some cases, the cleaving is performed before partitioning the cells into the barcode containing partitions. In some cases, the cleaving is performed after partitioning the cells into the barcode containing partitions. In some cases, the cleaving is performed simultaneously with the partitioning the cells into the barcode containing partitions. For example, simultaneous cleavage and partitioning of cells can be performed by partitioning the cells in the presence of a solution containing a cleavage reagent. In some embodiments, the oligonucleotides comprise one or more uracil nucleotides and cleaving comprising contacting the barcoded particles with a uracil DNA deglycosylase enzyme. In some cases, the oligonucleotides are disulfide linked to the barcoded particles, and cleavage comprises contacting the barcoded particles with a reducing agent.

In some cases, the template directed nucleic acid polymerization, or a reverse transcription, or a subsequent amplification is performed in the presence of a defined ratio of dUTP to dTTP, thereby incorporating U in the place of T at the defined ratio of U to T. In some cases, the ratio of U to T is about 1:2, 1/3, 1/4, 1/5, 1/6, 1/7, 1/8, 1/9, 1/10, 1/15, 1/20, 1/25, 1/30, 1/40, 1/50, 1/70, 1/75, 1/80, 1/90, 1/100, or less. In some cases, the ratio is 1:2, 1/3, 1/4, 1/5, 1/6, 1/7, 1/8, 1/9, 1/10, 1/15, 1/20, 1/25, 1/30, 1/40, 1/50, 1/70, 1/75, 1/80, 1/90, or 1/100. In some cases, the cDNA or an amplicon of the nucleic acid of the single cell is then fragmented by contacting with UDG/ApeI. In some cases, the fragments are contacted with a terminal transferase to add a polynucleotide end to the 5' or 3' end of the fragments. In some cases, the polynucleotide ends are hybridized to adaptor oligonucleotides. The adaptor oligonucleotides can be conjugated to the nucleic acid of the single cell by polymerization and/or ligation.

In another aspect, the present invention provides, a plurality of partitions, the partitions comprising: hydrogel; a linear polyacrylamide oligonucleotide conjugate; a bifunctional barcode template nucleic acid having a barcode region, a first end comprising a forward primer binding site and a second end comprising a reverse primer binding site; and a labeled reverse primer comprising a capture region and a primer region, wherein the primer region hybridizes to the reverse primer binding site of the second end of the bifunctional barcode template nucleic acid, wherein the linear polyacrylamide oligonucleotide conjugate comprises a forward primer that hybridizes to the forward primer binding site of the first end of the bifunctional barcode template nucleic acid, and wherein the barcode region of the bifunctional barcode template nucleic acid comprises a unique sequence in each partition. In some cases, the labeled reverse primer comprises a unique molecular barcode. In some cases, each partition comprises a plurality of labeled reverse primers, wherein the labeled reverse primers comprise unique molecular barcodes. In some embodiments, the bifunctional barcode template nucleic acid is double stranded. In some embodiments, the bifunctional barcode template nucleic acid is single-stranded.

In another aspect, the present invention provides a plurality of partitions, each partition comprising: hydrogel; and a linear polyacrylamide oligonucleotide conjugate, wherein the linear polyacrylamide oligonucleotide conjugate comprises a single stranded, bifunctional barcode template nucleic acid having a barcode region, a first end conjugated to the linear polyacrylamide, and a second end comprising a capture region, and wherein the barcode region of the bifunctional barcode template nucleic acid comprises a unique sequence in each partition (e.g., a unique or substantially unique partition-specific barcode). In some cases, partitions contain a unique or substantially unique partition-specific barcode sequence that is the same or substantially the same among all partition-specific barcodes in a partition, but unique or substantially unique as compared to the partition-specific barcode sequences of other partitions. Individual partitions can contain at least 10, 100; 200; 300; 500; 750; 1000; 2500; 5000; 7,500; 10,000; 15,000; 20,000; 30,000; 50,000; 100,000; $1\times10^6$; $1\times10^7$; or more copies of a partition-specific barcode that are identical or substantially identical in the partition-specific barcode sequence of a partition, and unique or substantially unique as compared to the partition-specific barcodes in other partitions. In some cases, the linear polyacrylamide oligonucleotide conjugate further comprises a second barcode region, wherein the second barcode region comprises a molecular barcode.

In some embodiments, the capture region comprises a poly-A nucleotide sequence or a poly-T nucleotide sequence. In some embodiments, the capture region can comprise a nucleotide sequence comprising a portion of a sequence of a target nucleic acid, or the reverse complement thereof. In some embodiments, the labeled reverse primer is labeled with a biotin molecule or a derivative thereof.

In some embodiments, less than about 10%, 1%, 0.1%, or fewer of the partitions comprise more than one unique barcode sequence, or more than one unique first barcode sequence (e.g., unique partition-specific barcode). In some embodiments, the partitions further comprise DNA amplification reagents.

In some embodiments, the partitions comprise hydrogel and each of the partitions further comprise a single cell. In some embodiments, the partitions comprise sol hydrogel and each of the partitions further comprise nucleic acid from a single cell. In some embodiments, the partitions comprise gel hydrogel and each of the partitions further comprise nucleic acid from a single cell. In some cases, the partitions further comprise template directed nucleic acid polymerization reagents. For example, template directed nucleic acid polymerization reagents can comprise reagents for performing reverse transcription.

In some embodiments, the plurality comprises at least 100; 200; 300; 500; 750; 1000; 2500; 5000; 7500; 10,000; 15,000; 20,000; 30,000, or more partitions. In some cases, the plurality has at least 10,000 partitions, each containing no more than one unique barcode sequence (e.g., no more than one unique partition-specific barcode sequence). The partitions can contain a unique or substantially unique partition-specific barcode sequence that is the same or substantially the same among all partition-specific barcodes in a partition, but unique or substantially unique as compared to the partition-specific barcode sequences of other partitions. Individual partitions can contain at least 10, 100; 200; 300; 500; 750; 1000; 2500; 5000; 7,500; 10,000; 15,000; 20,000; 30,000; 50,000; 100,000; $1\times10^6$; $1\times10^7$; or more copies of a partition-specific barcode that are identical or substantially identical in the partition-specific barcode sequence of a partition, and unique or substantially unique as compared to the partition-specific barcodes in other partitions.

In another, the present invention provides a method of making any of the foregoing plurality of partitions, the method comprising: mixing sol hydrogel and a linear polyacrylamide oligonucleotide conjugate in the presence of: labeled reverse primer, DNA polymerization and/or amplification reagents, and a bifunctional barcode template nucleic acid having a barcode region (e.g., a partition-specific barcode region), a first end comprising a forward primer binding site and a second end comprising a reverse primer binding site to form a mixture, and partitioning the mixture, wherein the bifunctional barcode template is present at a concentration such that at least about 90% 99.5%, or more of the plurality of partitions contain no more than one unique barcode sequence (e.g., no more than one unique partition-specific barcode sequence). In some cases, the labeled reverse primer contains a molecular barcode and each of the plurality of partitions contain a plurality of unique molecular barcode sequences.

In some embodiments, the bifunctional barcode template nucleic acid is a single-stranded bifunctional barcode template nucleic acid. In some embodiments, the method further comprises performing DNA amplification in the partitions to amplify the bifunctional barcode template nucleic acid and covalently link the bifunctional barcode template nucleic acid to the linear polyacrylamide oligonucleotide conjugate. In some embodiments, the method further comprises hardening the sol hydrogel to a gel form to generate a plurality of labeled hydrogel particles, each comprising a linear acrylamide oligonucleotide conjugate, wherein the linear polyacrylamide oligonucleotide conjugate is covalently linked to the bifunctional barcode template nucleic acid, and wherein the labeled hydrogel particles each contain a unique barcode sequence (e.g., each contain a unique partition-specific barcode sequence). In some cases, the labeled hydrogel particles each contain a plurality of molecular barcode sequences.

In some embodiments, the method further comprises combining the partitions and obtaining labeled hydrogel particles, each containing a unique barcode sequence (e.g., each containing a unique partition-specific barcode sequence). In some cases, the method further comprises separating the hydrogel particles from the label, wherein the separating comprises generating hydrogel particles comprising a linear polyacrylamide oligonucleotide conjugate covalently linked to a single stranded, bifunctional, barcode template nucleic acid. In some cases, the separating comprises contacting the labeled hydrogel particle with a nucleic acid denaturant and washing the label from the hydrogel particle. In some cases, the denaturant is an alkaline hydroxide.

In some cases, the method further comprises forming a plurality of partitions, each partition comprising a single cell and one of the hydrogel particles comprising a linear polyacrylamide oligonucleotide conjugate covalently linked to a single stranded, bifunctional, barcode template nucleic acid, the barcode template nucleic acid having a unique barcode sequence (e.g., a unique partition-specific barcode sequence). In some cases, the forming the plurality of partitions each comprising the single cell and the hydrogel particle is performed in the presence of template directed nucleic acid polymerization reagents. In some cases, the method further comprises lysing the single cells in the partitions.

In another aspect, the present invention provides a high-throughput method for single cell analysis comprising: performing any one of the foregoing methods at least 100; 200; 300; 500; 750; 1000; 2500; 5000; 7500; 10,000; 15,000; 20,000; 30,000; 50,000; 75,000; 100,000; 250,000; 500,000; $1\times10^6$ or more times in parallel; performing template directed nucleic acid polymerization or ligation, thereby covalently attaching the linear polyacrylamide oligonucleotide conjugate comprising the single stranded, bifunctional, barcode template nucleic acid to at least a portion of the nucleic acid of the single cell; combining the partitions before or after template directed polymerization or ligation; and performing high throughput sequencing.

In another aspect, the present invention provides a hydrogel particle, wherein the particle comprises: hydrogel; and a linear polyacrylamide oligonucleotide conjugate, wherein the linear polyacrylamide oligonucleotide conjugate is encapsulated in the hydrogel matrix, and wherein the oligonucleotide conjugate comprises a single stranded, bifunctional barcode template nucleic acid having a barcode region, a first end conjugated to the linear polyacrylamide, and a second end comprising a capture region. In some cases, the linear polyacrylamide oligonucleotide conjugate comprises a first barcode region, wherein the first barcode is a cellular or particle barcode that is unique for every, or substantially every, hydrogel particle and a second barcode region, wherein the second barcode is a molecular barcode that is unique for every, or substantially every, barcoded oligonucleotide molecule.

In another aspect, the present invention provides a set of any one of the foregoing hydrogel particles, wherein each particle has a unique barcode sequence (e.g., a unique cellular or particle barcode sequence). In some embodiments, each particle has a unique, or substantially unique, cellular or particle barcode and each oligonucleotide conjugated to a hydrogel has a unique, or substantially unique, molecular barcode. The set can comprise at least 100; 200; 300; 500; 750; 1000; 2500; 5000; 7500; 10,000; 15,000; 20,000; 30,000; 50,000; 75,000; 100,000; 250,000; 500,000; $1\times10^6$ or more hydrogel particles, wherein each particle has a unique or substantially unique barcode sequence (e.g., a unique cellular or particle barcode sequence). Individual particles can comprise at least 10, 100; 200; 300; 500; 750; 1000; 2500; 5000; 7,500; 10,000; 15,000; 20,000; 30,000; 50,000; 100,000; $1\times10^6$; $1\times10^7$; or more copies of the cellular or particle barcode.

In another aspect, the present invention provides a method of analyzing the nucleic acid of a single cell, the method comprising: forming a partition containing any one of the foregoing hydrogel particles; a single cell; and reagents for template directed nucleic acid polymerization; lysing the single cell; performing template directed nucleic acid polymerization, thereby covalently attaching the linear polyacrylamide oligonucleotide conjugate comprising the single stranded, bifunctional, barcode template nucleic acid to at least a portion of the nucleic acid of the single cell, or complementary DNA (cDNA) thereof; and sequencing the nucleic acid or cDNA of the single cell. In some cases, the template directed nucleic acid polymerization, or reverse transcription, or a subsequent amplification step is performed in the presence of a defined ratio of dUTP to dTTP, thereby incorporating U in the place of T at the defined ratio of U to T. In some cases, the ratio of U to T is about 1:2, 1/3, 1/4, 1/5, 1/6, 1/7, 1/8, 1/9, 1/10, 1/15, 1/20, 1/25, 1/30, 1/40, 1/50, 1/70, 1/75, 1/80, 1/90, 1/100, or less. In some cases, the ratio is 1:2, 1/3, 1/4, 1/5, 1/6, 1/7, 1/8, 1/9, 1/10, 1/15, 1/20, 1/25, 1/30, 1/40, 1/50, 1/70, 1/75, 1/80, 1/90, or 1/100. In some cases, the cDNA or an amplicon of the nucleic acid of the single cell is then fragmented by contacting with UDG/ApeI. In some cases, the fragments are contacted with a terminal transferase to add a polynucleotide end to the 5' or 3' end of the fragments. In some cases, the polynucleotide ends are hybridized to adaptor oligonucleotides. The adaptor oligonucleotides can be conjugated to the nucleic acid of the single cell by polymerization and/or ligation.

In another aspect, the present invention provides a high throughput method of individually analyzing the nucleic acid of a plurality of cells in parallel, the method comprising: providing a suspension of any of the foregoing hydrogel particles; forming a plurality of partitions, wherein each partition comprises: a hydrogel particle comprising: hydrogel; and a linear polyacrylamide oligonucleotide conjugate, wherein the linear polyacrylamide oligonucleotide conjugate is encapsulated in the hydrogel matrix, and wherein the oligonucleotide conjugate comprises a single stranded, bifunctional barcode template nucleic acid having a unique barcode region (e.g., a unique cellular or partition-specific barcode region), a first end conjugated to the linear polyacrylamide, and a second end comprising a capture region; a single cell; and template directed nucleic acid polymerization reagents; lysing the single cells; performing template directed nucleic acid polymerization, thereby covalently attaching the linear polyacrylamide oligonucleotide conjugate comprising the single stranded, bifunctional, barcode template nucleic acid having a unique barcode region of each partition mixture to at least a portion of the nucleic acid, or cDNA, of the single cell of each partition mixture, to form unique barcoded nucleic acid, or cDNA, of the single cell in each partition; combining the partitions; and performing high throughput sequencing of barcoded nucleic acid, wherein sequences having the same barcode (e.g., the same cellular or partition-specific barcode) originate from the same single cell and/or from the same single partition. In some cases, the linear polyacrylamide oligonucleotide conjugate further comprises a plurality of unique molecular barcodes. In some cases, sequences having the same molecular barcode originate from the same nucleic acid molecule.

In some embodiments, the plurality of partitions comprises at least 100; 200; 300; 500; 750; 1000; 2500; 5000; 7500; 10,000; 15,000; 20,000; 30,000; 50,000; 75,000; 100,000; 250,000; 500,000; $1\times10^6$ or more partitions. In some cases, wherein the template directed nucleic acid polymerization reagents comprise reverse transcription reagents. In some cases, the lysing the single cells comprises equilibrating the plurality of partitions to a temperature that melts the hydrogel particles. In some cases, the equilibrating comprises heating the plurality of partitions and melting the hydrogel particles.

In some cases, the template directed nucleic acid polymerization, or reverse transcription, or a subsequent amplification step is performed in the presence of a defined ratio of dUTP to dTTP, thereby incorporating U in the place of T at the defined ratio of U to T. In some cases, the ratio of U to T is about 1:2, 1/3, 1/4, 1/5, 1/6, 1/7, 1/8, 1/9, 1/10, 1/15, 1/20, 1/25, 1/30, 1/40, 1/50, 1/70, 1/75, 1/80, 1/90, 1/100, or less. In some cases, the ratio is 1:2, 1/3, 1/4, 1/5, 1/6, 1/7, 1/8, 1/9, 1/10, 1/15, 1/20, 1/25, 1/30, 1/40, 1/50, 1/70, 1/75, 1/80, 1/90, or 1/100. In some cases, the cDNA or an amplicon of the nucleic acid of the single cell is then fragmented by contacting with UDG/ApeI. In some cases, the fragments are contacted with a terminal transferase to add a polynucleotide end to the 5' or 3' end of the fragments. In some cases, the polynucleotide ends are hybridized to adaptor oligonucleotides. The adaptor oligonucleotides can be conjugated to the nucleic acid of the single cell by polymerization and/or ligation.

In any of the foregoing aspects, embodiments, cases, or examples, the hydrogel can comprise agarose.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well-known and commonly employed in the art.

The term "amplification reaction" refers to any in vitro means for multiplying the copies of a target sequence of nucleic acid in a linear or exponential manner. Such methods include but are not limited to polymerase chain reaction (PCR); DNA ligase chain reaction (see U.S. Pat. Nos. 4,683,195 and 4,683,202; PCR Protocols: A Guide to Methods and Applications (Innis et al., eds, 1990)) (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3SR); isothermal amplification reactions (e.g., single-primer isothermal amplification (SPIA)); as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing or linear amplification.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. Amplification reaction mixtures may also further include stabilizers and other additives to optimize efficiency and specificity. Depending upon the context, the mixture can be either a complete or incomplete amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra. Primers can be DNA, RNA, or a chimera of DNA and RNA portions. In some cases, primers can include one or more modified or non-natural nucleotide bases. In some cases, primers are labeled.

A nucleic acid, or a portion thereof, "hybridizes" to another nucleic acid under conditions such that non-specific hybridization is minimal at a defined temperature in a physiological buffer (e.g., pH 6-9, 25-150 mM chloride salt). In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 14, 16, or 18 contiguous complementary nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C. In some embodiments, the defined temperature at which specific hybridization occurs is 37, 40, 42, 45, 50, 55, 60, 65, 70, 75, or 80° C.

A "template" refers to a polynucleotide sequence that comprises the polynucleotide to be amplified, flanked by or a pair of primer hybridization sites. Thus, a "target template" comprises the target polynucleotide sequence adjacent to at least one hybridization site for a primer. In some cases, a "target template" comprises the target polynucleotide sequence flanked by a hybridization site for a "forward" primer and a "reverse" primer.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

The term "long fragment DNA" refers to target DNA having a length of at least about 300; 400; 500; 600; 700; 800; 1,000; or more bases (or base pairs for double stranded target DNA). Long fragment DNA can be a particularly advantageous substrate for obtaining "phased" sequencing information from a genome. A phased genomic sequence refers to a sequence where sequence information can be assigned to a specific chromatid from an individual.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

A "polymerase" refers to an enzyme that performs template-directed synthesis of polynucleotides, e.g., DNA and/or RNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis*, and *Thermotoga maritime*, or modified versions thereof.

Additional examples of commercially available polymerase enzymes include, but are not limited to: Klenow fragment (New England Biolabs® Inc.), Taq DNA polymerase (QIAGEN), 9 °N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.).

Polymerases include both DNA-dependent polymerases and RNA-dependent polymerases such as reverse transcriptase. At least five families of DNA-dependent DNA polymerases are known, although most fall into families A, B and C. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

The terms "label," "detectable label, "detectable moiety," and like terms refer to a composition detectable by spectroscopic, photochemical, biochemical, immunochemical, chemical, or other physical means. For example, useful labels include fluorescent dyes (fluorophores), luminescent agents, electron-dense reagents, enzymes (e.g., as commonly used in an ELISA), biotin, digoxigenin, $^{32}$P and other isotopes, haptens, and proteins which can be made detectable, e.g., by incorporating a radiolabel into the peptide or used to detect antibodies specifically reactive with the peptide. The term includes combinations of single labeling agents, e.g., a combination of fluorophores that provides a unique detectable signature, e.g., at a particular wavelength or combination of wavelengths. Any method known in the art for conjugating label to a desired agent may be employed, e.g., using methods described in Hermanson, *Bioconjugate Techniques* 1996, Academic Press, Inc., San Diego.

As used herein, the term "partitioning" or "partitioned" refers to separating a sample into a plurality of portions, or "partitions." Partitions are generally physical, such that a sample in one partition does not, or does not substantially, mix with a sample in an adjacent partition. Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

In some cases partitions are virtual. In a preferred embodiment, virtual partitions require a physical alteration of a molecule or group of molecules, wherein the alteration identifies a unique partition for that molecule or group of molecules. Typical physical alterations suitable for establishing or maintaining virtual partitioning include, without limitation, nucleic acid barcodes, detectable labels, etc. For example, a sample can be physically partitioned, and the components of each partition tagged with a unique identifier (e.g., a unique nucleic acid sequence barcode) such that the identifier is unique as compared to other partitions but shared between the components of the partition. The unique identifier can then be used to maintain a virtual partition in downstream applications that involve combining of the physically partitioned material. Thus, if the sample is a sample of cells physically partitioned into partitions containing a single cell, the identifier can identify different nucleic acids that derived from a single cell after partitions are recombined.

As used herein, the term "gel" refers to a substantially dilute network of cross-linked material. A "hydrogel" is a gel in which the liquid component is water. Gels and hydrogels can be deformable. Gels and hydrogels can be in a sol (liquid) or gel (solid) form. In some cases, hydrogels are reversible. Reversible hydrogels can be reversibly transitioned between a sol (liquid) or gel (solid) form. For example, agarose hydrogel can be transitioned into a sol form with heat and a gel form with cooling. Alternatively, some hydrogel compositions exist in a sol form below a transition temperature and a gel form above the transition temperature. In some cases, a sol (liquid) hydrogel, or hydrogel precursor, can be irreversibly hardened into a gel form. For example, acrylamide can be irreversibly polymerized into a gel form. As used herein, sol refers to either the soluble form of a hydrogel, or soluble hydrogel precursor, and gel refers to a solid hydrogel. Numerous reversible and irreversible hydrogel compositions are known in the art, including those described in, e.g., U.S. Pat. Nos. 4,438,258; 6,534,083; 8,008,476; 8,329,763; U.S. Patent Appl. Nos. 2002/0,009,591; 2013/0,022,569; 2013/0,034,592; and International Patent Publication Nos. WO/1997/030092; and WO/2001/049240.

As used herein a "barcode" is a short nucleotide sequence (e.g., at least about 4, 6, 8, 10, or 12, nucleotides long) that identifies a molecule to which it is conjugated. Barcodes can be used, e.g., to identify molecules in a partition. Such a partition-specific barcode should be unique for that partition as compared to barcodes present in other partitions. For example, partitions containing target RNA from single-cells can subject to reverse transcription conditions using primers that contain a different partition-specific barcode sequence in each partition, thus incorporating a copy of a unique "cellular barcode" into the reverse transcribed nucleic acids of each partition. Thus, nucleic acid from each cell can be distinguished from nucleic acid of other cells due to the unique "cellular barcode." In some cases, the cellular barcode is provided by a "particle barcode" that is present on oligonucleotides conjugated to a particle, wherein the particle barcode is shared by (e.g., identical or substantially identical amongst) all, or substantially all, of the oligonucleotides conjugated to that particle. Thus, cellular and particle barcodes can be present in a partition, attached to a particle, or bound to cellular nucleic acid as multiple copies of the same barcode sequence. Cellular or particle barcodes of the same sequence can be identified as deriving from the same cell, partition, or particle. Such partition-specific, cellular, or particle barcodes can be generated using a variety of methods, which methods result in the barcode conjugated to or incorporated into a solid or hydrogel support (e.g., a solid bead or particle or hydrogel bead or particle). In some cases, the partition-specific, cellular, or particle barcode is generated using a split and mix (also referred to as split and pool) synthetic scheme as described herein. A partition-specific barcode can be a cellular barcode and/or a particle barcode. Similarly, a cellular barcode can be a partition specific barcode and/or a particle barcode. Additionally, a particle barcode can be a cellular barcode and/or a partition-specific barcode.

In other cases, barcodes uniquely identify the molecule to which it is conjugated. For example, by performing reverse transcription using primers that each contain a unique "molecular barcode." In still other examples, primers can be utilized that contain "partition-specific barcodes" unique to each partition, and "molecular barcodes" unique to each molecule. After barcoding, partitions can then be combined, and optionally amplified, while maintaining virtual partitioning. Thus, e.g., the presence or absence of a target nucleic acid (e.g., reverse transcribed nucleic acid) comprising each barcode can be counted (e.g. by sequencing) without the necessity of maintaining physical partitions.

The length of the barcode sequence determines how many unique samples can be differentiated. For example, a 1 nucleotide barcode can differentiate 4, or fewer, different samples or molecules; a 4 nucleotide barcode can differentiate $4^4$ or 256 samples or less; a 6 nucleotide barcode can differentiate 4096 different samples or less; and an 8 nucleotide barcode can index 65,536 different samples or less. Additionally, barcodes can be attached to both strands either through barcoded primers for both first and second strand synthesis or through ligation.

Barcodes are typically synthesized and/or polymerized (e.g., amplified) using processes that are inherently inexact. Thus, barcodes that are meant to be uniform (e.g., a cellular, particle, or partition-specific barcode shared amongst all barcoded nucleic acid of a single partition, cell, or bead) can contain various N–1 deletions or other mutations from the canonical barcode sequence. Thus, barcodes that are referred to as "identical or substantially identical copies" refer to barcodes that differ due to one or more errors in, e.g., synthesis, polyermization, or purification and thus contain various N–1 deletions or other mutations from the canonical barcode sequence. Moreover, the random conjugation of barcode nucleotides during synthesis using e.g., a split and pool approach and/or an equal mixture of nucleotide precursor molecules as described herein, can lead to low probability events in which a barcode is not absolutely unique (e.g., different from other barcodes of a population or different from barcodes of a different partition, cell, or bead). However, such minor variations from theoretically ideal barcodes do not interfere with the single cell analysis methods, compositions, and kits described herein. Therefore, as used herein, the term "unique" in the context of a particle, cellular, partition-specific, or molecular barcode encompasses various inadvertent N–1 deletions and mutations from the ideal barcode sequence. In some cases, issues due to the inexact nature of barcode synthesis, polymerization, and/or amplification, are overcome by oversampling of possible barcode sequences as compared to the number of barcode sequences to be distinguished (e.g., at least about 2-, 5-, 10-fold or more possible barcode sequences). For example, 10,000 cells can be analyzed using a cellular barcode having 9 barcode nucleotides, representing 262,144 possible barcode sequences. The use of barcode technology is well known in the art, see for example Katsuyuki Shiroguchi, et al. Proc Natl Acad Sci USA., 2012 Jan. 24; 109(4):1347-52; and Smith, A M et al., Nucleic Acids Research Can 11, (2010).

DETAILED DESCRIPTION OF THE INVENTION

I. Introduction

Figure 1:
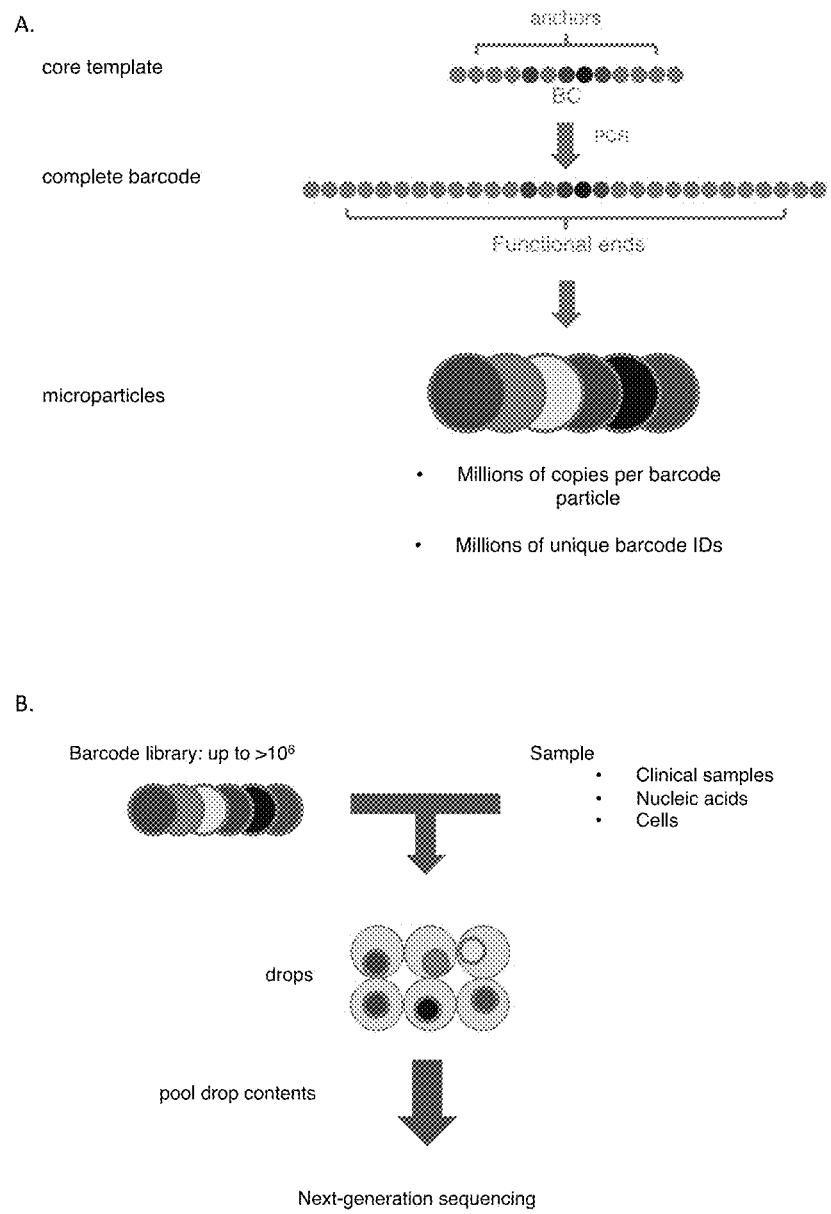
FIG. 1: Overview of a process for making and using barcoded hydrogel particles. A) The process depicted here utilizes an oligonucleotide with a degenerate core flanked by ends of known structure (anchors). The anchors are used to append functional sequences onto the degenerate core using PCR. The functional barcode is synthesized directly onto a hydrogel particle by amplifying the core template with at least one PCR primer that is covalently coupled to the hydrogel polymer. The primers and polymer encapsulated into droplets with a template at lower than 1 copy per droplet. PCR is performed in the droplet to amplify the template molecules. After amplification, the polymer is hardened into a particle. This results in millions of hydrogel particles, each with millions of copies of a unique functional DNA barcode. B) The barcode library can then be combined in another emulsion drop with an object to barcode, such as nucleic acids or cells. After the barcoding reaction, the drops can be pooled and subjected to downstream processing such as DNA sequencing.

Described herein are methods, compositions, and kits for analysis of nucleic acid. The methods, compositions, and kits can be used, e.g., for analysis of cells at the single-cell level. In some embodiments, the methods utilize a novel dual barcoded particle having a plurality of oligonucleotides, the plurality of oligonucleotides having a particle barcode that is the same or substantially the same among the plurality of oligonucleotides, and a molecular barcode that is, or is substantially, unique for each oligonucleotide. In a plurality of particles, the particle barcode can be the same or substantially the same among the plurality of oligonucleotides on a particle, but unique or substantially unique as compared to the plurality of oligonucleotides on other particles. The dual barcoded particles can be used, e.g., to barcode nucleic acid at the single cell level, wherein each nucleic acid has a barcode that uniquely identifies the source cell, and a molecular barcode that uniquely identifies the nucleic acid.

In some embodiments, the methods utilize a novel combination of bifunctional barcode template nucleic acids and two separate partitioning steps to barcode target nucleic acid (e.g., DNA or RNA) of a plurality of cells, such that the nucleic acid of each cell has a unique barcode. In some embodiments, the methods utilize a novel library of bifunctional barcoded hydrogel particles, wherein the bifunctional barcoded hydrogel particles contain a capture region for hybridizing to target nucleic acid (e.g., DNA or RNA) of a single cell in a partition and barcoding the nucleic acid.

The methods, compositions and kits described herein can be used for analysis of a variety of target nucleic acids. In some cases, single cell target nucleic acid (e.g., genomic DNA, RNA, mRNA, lncRNA, etc.) is analyzed. However, the methods compositions and kits are not limited to single cell analysis. For example, nucleic acid from a biological sample containing a plurality of cells can be extracted and partitioned such that individual partitions contain nucleic acid from less than one, one, or a plurality of cells. The partitioned nucleic acid can be barcoded using a barcoded particle (e.g., hydrogel particle or polymethylmethacrylate or polystyrene bead) as described herein. Suitable target nucleic acid substrates can include, but are not limited to, one or more of the following: long fragment DNA, cross-linked and/or circularized DNA fragments (e.g., from a 3C or 4C library), products of a branched DNA amplification; nucleic acid from single cells; nucleic acid from multicellular organisms such as *C. elegans* (See, e.g., Clausell-Tormos et al., Chem Biol. 2008 May; 15(5):427-37), spheroids (See, e.g., Fennema et al., Trends Biotechnol. 2013 February; 31(2):108-15), or exosomes (See, e.g., J Extracell Vesicles. 2015 May 29; 4:26760).

In some cases, single cell analysis of nucleic acid is accomplished by partitioning single cells and barcodes (e.g., barcoded particles), such that no, or substantially no, or less than about 10%, 1%, 0.1%, 0.01%, or 0.001% of the partitions contain more than one cell or more than one unique cellular or particle barcode sequence. In some cases, single cell analysis of nucleic acid is accomplished by partitioning single cells and barcoded particles, such that no, or substantially no, or less than about 10%, 1%, 0.1%, 0.01%, or 0.001% of the partitions contain more than one cell or more than one particle.

II. Compositions

In some embodiments, the present invention provides a plurality of partitions (e.g., at least 100; 200; 300; 500; 750; 1000; 2500; 5000; 7500; 10,000; 15,000; 20,000; 30,000, or more partitions), each partition having a unique barcode. The partitions can further contain template directed nucleic acid polymerization reagents and/or template directed nucleic acid polymerization products. Exemplary template directed nucleic acid polymerization reagents include polymerases (e.g., thermostable DNA-dependent polymerase, or RNA-dependent polymerase), nucleotides, buffers, salts, oligonucleotide primers etc. Template directed nucleic acid polymerization reagents further include reagents for performing reverse transcription. Exemplary template directed nucleic acid polymerization products include barcoded nucleic acid produced by template directed nucleic acid polymerization. The partitions can also, or alternatively, contain template directed nucleic acid ligation reagents and/or template directed nucleic acid ligation products. Exemplary template directed nucleic acid ligation reagents include ligases (e.g., DNA dependent ligases or RNA dependent ligases), nucleotides, buffers, salts, oligonucleotide primers etc. Exemplary template directed nucleic acid ligation products include barcoded nucleic acid produced by template directed nucleic acid ligation of a barcoded nucleotide released from a particle and ligated to a double stranded target nucleic acid. The plurality of partitions can each contain a single cell, or nucleic acid from a single cell. In some cases, the plurality of partitions can be useful for analyzing nucleic acid of a sample of cells at a single cell level.

A. Hydrogel

In some embodiments, the plurality of partitions, each partition having a unique partition-specific barcode, is produced using a hydrogel-based process. Thus, in some cases, the plurality of partitions contain: a hydrogel; a bifunctional barcode template nucleic acid having a barcode region, a forward primer binding site, and a reverse primer binding site; an oligonucleotide configured to link the hydrogel to the bifunctional barcode template; and a labeled reverse primer, the reverse primer having a capture region and a primer region, wherein the primer region, or a portion thereof, hybridizes to the reverse primer binding site of the bifunctional barcode template nucleic acid, or a portion thereof. The reverse primer can further contain a molecular barcode that uniquely identifies a molecule of reverse primer, or a polymerase extension product thereof. In some cases, the hydrogel is in sol form. In some cases, the hydrogel is in gel form. An exemplary hydrogel is an agarose hydrogel. Other hydrogels include, but are not limited to, those described in, e.g., U.S. Pat. Nos. 4,438,258; 6,534,083; 8,008,476; 8,329,763; U.S. Patent Appl. Nos. 2002/0,009,591; 2013/0,022,569; 2013/0,034,592; and International Patent Publication Nos. WO/1997/030092; and WO/2001/049240. In some cases, the oligonucleotide configured to link the hydrogel to the barcode contains a forward primer portion that hybridizes to the forward primer binding site of the bifunctional barcode template.

In some embodiments, the oligonucleotide configured to link the hydrogel to the barcode is covalently linked to the hydrogel. Numerous methods for covalently linking an oligonucleotide to one or more hydrogel matrices are known in the art. As but one example, aldehyde derivatized agarose can be covalently linked to a 5'-amine group of a synthetic oligonucleotide. Thus, in each partition, oligonucleotide covalently linked to the hydrogel and containing a forward primer portion can hybridize to the forward primer binding site of the bifunctional barcode template to form a plurality of partitions, each containing a hydrogel particle linked to an oligonucleotide. In such an embodiment, the hydrogel is further linked to the bifunctional barcode template due to hybridization between the forward primer portion of the oligonucleotide and the forward primer binding site of the bifunctional barcode template. In some cases, the forward primer portion of the oligonucleotide is a T7 primer, a portion thereof, or the reverse complement thereof.

In some embodiments, the oligonucleotide configured to link the hydrogel to the barcode is conjugated to a high molecular weight (e.g., at least about 5, 10, 15, 20, 25, 30, 35, 40, 50 kDa, or more) polymer that can be sterically constrained within a gel form hydrogel matrix. For example, the oligonucleotide can be conjugated to a high molecular weight linear or branched polyacrylamide. As another example, the oligonucleotide can be conjugated to a high molecular weight nucleic acid. The high molecular weight polymer oligonucleotide conjugate (e.g., linear polyacrylamide oligonucleotide conjugate) can be incorporated into a hydrogel matrix by mixing with sol hydrogel and hardening the hydrogel into gel form. In some cases, the plurality of the partitions contain an oligonucleotide conjugated to a high molecular weight linear or branched polyacrylamide, a hydrogel in sol form, and a bifunctional barcode template containing a unique partition-specific barcode. Other high molecular weight polymers are suitable for conjugation with an oligonucleotide and encapsulation into a hydrogel. Exemplary polymers include, but are not limited to, dextrans, chitosan, styrenated gelatin, hyaluronic acid, alginate, gelatin, polyethylene glycols, and derivatives thereof.

In some cases, the oligonucleotide is conjugated into a linear polyacrylamide by forming a reaction mixture containing one or more acrydite-oligonucleotides and a plurality of acrylamide monomers and polymerizing the reaction mixture to generate a linear polyacrylamide-oligonucleotide conjugate. The reaction can be performed to generate a plurality of linear polyacrylamide-oligonucleotide conjugates. The mean number of oligonucleotides incorporated into the linear polyacrylamide molecules can be controlled by altering the reaction conditions. For example the following non-limiting reaction conditions can be altered to control the average number of incorporated oligonucleotides: pH; temperature; incident light intensity; time of the polymerization reaction; or concentration of oligonucleotide, acrylamide monomer, catalyst (e.g., TEMED), or initiator (e.g., riboflavin or ammonium persulfate).

The bifunctional barcode template can be amplified using the forward primer and/or a reverse primer (e.g., labeled reverse primer, or a labeled reverse primer having a molecular barcode). The hydrogel can then be hardened to form a plurality of partitions, each containing a hydrogel particle linked to, or encapsulating, an oligonucleotide. In some cases, the hydrogel is in sol form during amplification and hardened to a gel form after amplification. In some cases, the binding of forward and/or reverse primers and amplification transforms the bifunctional barcode template from a single stranded nucleic acid molecule to a double stranded nucleic acid molecule. In some cases, the forward primer portion of the oligonucleotide is a T7 primer, a portion thereof, or the reverse complement thereof. In some cases, amplification with a labeled reverse primer provides a labeled bifunctional barcode nucleic acid. In some cases, the label is a biotin label, or a derivative thereof.

In some cases, the oligonucleotide can contain a forward primer portion that hybridizes to the forward primer binding site of the bifunctional barcode template. Thus, in this embodiment, the oligonucleotide links the hydrogel particle to the bifunctional barcode template by hybridization and/or subsequent polymerization from the forward primer.

The bifunctional barcode template contains a barcode region. The barcode region can contain at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 barcode nucleotides. For example, a barcode region of 20 nucleotides can uniquely identify nucleic acid from $4^{20}$ different cells. In some cases, the barcode region contains from about 5 to about 25 barcode nucleotides, from about 8 to about 20 barcode oligonucleotides, or from about 10 to about 14 barcode oligonucleotides.

In some cases, the bifunctional barcode template also contains a forward primer binding site and a reverse primer binding site. The forward primer binding site hybridizes to the forward primer, or portion thereof, of the oligonucleotide configured to link the hydrogel to the bifunctional barcode template. In some embodiments, the bifunctional barcode template contains, from a 5' end to a 3' end, the forward primer binding site, the unique partition-specific or hydrogel particle barcode, and the reverse primer binding site. In some cases, the forward primer binding site is a binding site for a T7 primer, or portion thereof. In some cases, the forward primer binding site is the reverse complement of a T7 primer sequence, or a portion thereof. In some cases, the reverse primer binding site hybridizes to the primer region, or portion thereof, of the labeled reverse primer.

In some embodiments, the bifunctional barcode template can contain additional nucleic acid sequences to provide a specified functionality. For example, the bifunctional barcode template can contain one or more additional primer binding sites, barcodes (e.g., molecular or partition-specific), or one or more labels. In some cases, the one or more additional primer binding sites are sequencing primer binding sites.

In some cases, the bifunctional barcode template is introduced into a partition as a single stranded nucleic acid, linked to hydrogel via the oligonucleotide configured to link hydrogel to the bifunctional barcode template, and transformed into a double stranded nucleic acid via a polymerase. For example, the bifunctional barcode template can be amplified using a forward and/or reverse primer. In some cases, the amplification product contains a partition-specific barcode provided by the bifunctional barcode template and a molecular barcode provided by a labeled reverse primer having a molecular barcode.

In some cases, the reverse primer contains a primer region that hybridizes to the reverse primer binding site of the bifunctional barcode template and a capture region. The capture region can be any sequence in which the reverse complement thereof is capable of capturing (e.g., hybridizing to) a target nucleic acid or a plurality of target nucleic acids of interest. For example, the capture region can be a poly-adenine nucleotide sequence (e.g., 10-25 or more contiguous adenine nucleotides). As another example, the reverse complement of the capture region can hybridize to a conserved region of a gene family. As yet another example, the reverse complement of the capture region can hybridize to a sequence containing two contiguous exons, and thus detect mature RNA expressed from a specific gene or gene family. In some cases, the capture region of the reverse primer contains one or more inosine, nitroindole, or other universal nucleotides.

The capture region can be linked to the hydrogel by hybridizing the primer region of the forward primer to the bifunctional barcode template. Primer initiated and template directed polymerization of the forward and reverse primers can then incorporate the reverse complement of the capture region. In some cases, the primer initiated and template directed polymerization of the reverse and forward primers incorporates the reverse complement of the capture region and a molecular barcode. In such cases, the hydrogel will thereby be covalently linked to the capture region. For example, the hydrogel can thereby be covalently linked to a poly-thymine sequence (e.g., 10-25 or more contiguous thymine nucleotides) for capturing mRNA from a cell.

In some embodiments, less than about 10%, 1%, 0.1%, 0.05%, 0.01%, 0.005%, 0.001% or fewer of the plurality of partitions contain more than one unique barcode or unique barcode sequence (e.g., partition-specific barcode sequence). In some embodiments, the plurality of partitions contains at least 1,000; 5,000; 10,000; 15,000; 20,000; or 30,000; partitions, each partition containing no more than 1 unique partition-specific barcode sequence. In some embodiments, the plurality of partitions contains at least 1,000; 5,000; 10,000; 15,000; 20,000; or 30,000; partitions, wherein at least 90%, 95%, or more of the partitions contain a unique partition-specific barcode sequence. For example, a sample containing a dilute solution of bifunctional barcode template nucleic acids can be partitioned. Alternatively, the number of partitions a sample is partitioned into can be greater than the number of molecules of bifunctional barcode template nucleic acid. Individual partitions can contain at least 10, 100; 200; 300; 500; 750; 1000; 2500; 5000; 7,500; 10,000; 15,000; 20,000; 30,000; 50,000; 100,000; $1\times10^6$; $1\times10^7$; or more copies of a partition-specific barcode that are identical or substantially identical in the partition-specific barcode sequence of a partition, and unique or substantially unique as compared to the partition-specific barcodes in other partitions.

In some cases, the partitioning provides partitions that do not contain any bifunctional barcode template nucleic acids, and thus do not contain a barcode. Such partitions are referred to as "empty" partitions, though one of skill in the art will appreciate that the partitions can contain other molecules, including but not limited to template directed nucleic acid polymerization reagents, or target nucleic acid.

In some cases, empty partitions can be separated from partitions containing a barcode. For example, the bifunctional barcode template nucleic acid can be amplified using forward and/or reverse primers in each partition. Partitions can then be segregated based on the presence or absence of an amplified product using methods know in the art. For example, increased fluorescence of an intercalating dye can be detected.

In some cases, the plurality of partitions are combined (e.g., before or after amplification) when the hydrogel is in gel form to obtain hydrogel particles, and barcoded particles are separated from those that do not have a barcode. For example, particles containing a label corresponding to the labeled reverse primer (e.g., a biotin label) can be separated from partitions that do not contain the label using methods known in the art.

In some embodiments, the plurality of partitions have a unique barcoded (e.g., each partition has a unique partition-specific barcoded) hydrogel (e.g., sol or gel) and further contain a single cell, nucleic acid from a single cell, or nucleic acid from a plurality of cells, in each partition. For example, a plurality of hydrogel particles in gel form can be provided, the particles each containing a unique barcode (e.g., a unique particle barcode). The particles can be mixed with a plurality of cells and partitioned to form a plurality of partitions having a barcoded hydrogel particle and a single cell or nucleic acid from a single cell. Alternatively, a plurality of partitions each with a single cell can be formed, the cells optionally lysed, and barcoded particles (e.g., particles, each having a particle barcode) then incorporated into the plurality of partitions. As yet another alternative, a plurality of partitions each with a barcoded hydrogel (e.g., each with a unique particle barcode) can be formed and cells incorporated therein. As yet another alternative, a plurality of partitions, each with a barcoded hydrogel, and a plurality of partitions, each containing a single cell or nucleic acid from a single cell, can be formed. The barcoded hydrogel containing partitions can then be combined with the single cell/nucleic acid containing partitions to form a plurality of partitions containing a barcoded hydrogel and a single cell or nucleic acid from a single cell. Generally, these methods are performed such that the majority, the vast majority, at least 90%, 95%, 99%, or more of the partitions each contain a single unique partition-specific barcode sequence. For example, each partition can contain from one to millions of copies or more of a single unique partition-specific barcode sequence. In some cases, the partitions also contain unique molecular barcode sequences that are unique, or substantially unique, for reach molecular barcoded nucleic acid molecule therein.

In some cases, the partitions can be subjected to a lysis condition to lyse the cells in the partitions, thereby forming a plurality of partitions having a barcoded hydrogel particle and nucleic acid from a single cell. In some cases, the partitions can be heated to lyse the cells and melt the hydrogel, thereby forming a plurality of partitions having sol hydrogel and nucleic acid from a single cell.

In some embodiments, the present invention provides a hydrogel particle, wherein the particle comprises hydrogel in gel form and an oligonucleotide having a single-stranded bifunctional barcode template nucleic acid, wherein the first end of the bifunctional barcode is conjugated to the hydrogel or conjugated to a linear polyacrylamide encapsulated in the hydrogel matrix, and a second end having a capture region. In some cases, the present invention provides a set of such particles (e.g., at least 100; 200; 300; 500; 750; 1000; 2500; 5000; 7500; 10,000; 15,000; 20,000; 30,000; 50,000; 75,000; 100,000; 250,000; 500,000; $1 \times 10^6$ or more hydrogel particles), each particle having a unique barcode sequence.

The capture region can be any sequence in which the reverse complement thereof is capable of capturing (e.g., hybridizing to) a target nucleic acid or a plurality of target nucleic acids of interest. For example, the capture region can be a poly-adenine nucleotide sequence (e.g., 10-25 or more contiguous adenine nucleotides). As another example, the reverse complement of the capture region can hybridize to a conserved region of a gene family. As yet another example, the reverse complement of the capture region can hybridize to a sequence containing two contiguous exons, and thus detect mature RNA expressed from a specific gene or gene family. In some cases, the capture region of the reverse primer contains one or more inosine, nitroindole, or other universal nucleotides.

In some cases, the bifunctional barcode of the hydrogel particle, or set of hydrogel particles, can further contain primer binding sites. For example, a T7 primer binding site or reverse complement thereof can be included for unbiased amplification of target nucleic acid. As another example, the bifunctional barcode can include one or more sequencing primer binding sites, or the reverse complement thereof.

B. Barcoded Particles or Partitions that do not Require Hydrogel

In some embodiments, barcoded particles, or partitions containing such barcoded particles are provided that do not require hydrogel. For example, barcodes can be synthesized onto solid support particles using standard oligonucleotide synthesis methods. In some cases, the barcoded particles (e.g., at least 100; 200; 300; 500; 750; 1000; 2500; 5000; 7500; 10,000; 15,000; 20,000; 30,000; 50,000; 75,000; 100,000; 250,000; 500,000; or $1 \times 10^6$ particles) contain unique particle barcodes. For example, each particle can contain a plurality of oligonucleotides, wherein each oligonucleotide of that particle contains the same, or substantially the same, barcode sequence. In some cases, partitioning of the barcoded particles, such that all, substantially all, or at least 90%, 95%, 99%, or more of the partitions contain no more than 1 particle, provides a plurality of partitions containing unique barcodes.

In some cases a barcoded particle includes a solid support surface, the solid support surface having a plurality of oligonucleotides conjugated thereon, wherein the plurality of oligonucleotides comprise: a first defined region having a defined sequence of 10-100 nucleotides; and a particle barcode having 6-20 nucleotides, wherein all, substantially all, or a majority of the plurality of oligonucleotide primers contain the same particle barcode sequence. In some cases, the barcoded particle contains from 3' to 5' the first defined region, and the particle barcode. In other cases, the barcoded particle contains from 5' to 3' the first defined region, and the particle barcode.

In some cases, a dual barcoded particle is provided. For example, a dual barcoded particle can contain a plurality of oligonucleotides, each oligonucleotide containing a cellular/particle barcode unique to that particle and a plurality of molecular barcodes unique to each oligonucleotide. In some cases a dual barcoded particle includes a solid support surface, the solid support surface having a plurality of oligonucleotides conjugated thereon, wherein the plurality of oligonucleotides comprise: a first defined region having a defined sequence of 10-100 nucleotides; a particle barcode having 6-20 nucleotides, wherein all, substantially all, or a majority of the plurality of oligonucleotides contain the same particle barcode sequence; and a molecular barcode having 6-20 nucleotides, wherein all, or substantially all, of the plurality of oligonucleotide primers have a unique molecular barcode. In some cases, the dual barcoded particle contains from 3' to 5' the first defined region, the particle barcode, and the molecular barcode. In other cases, the dual barcoded particle contains from 5' to 3' the first defined region, the particle barcode, and the molecular barcode. One of skill in the art will appreciate that the relative location of the particle barcode and the molecular barcode can be altered. For example, in some cases, the dual barcoded particle contains the particle barcode 5' of the molecular barcode. In other cases, the dual barcoded particle contains the particle barcode 3' of the molecular barcode.

In some cases, the plurality of oligonucleotides of the barcoded particle or dual barcoded particle contain a cleavage region. For example, the cleavage region can be proximal to a solid support. Thus, the cleavage region can be configured to enable cleavage of the oligonucleotides from the solid support. In some cases, the cleavage region contains at least one uracil nucleotide. In some cases, the cleavage region contains an endonuclease recognition site.

In some cases, the cleavage region is an acid or base labile bond. In some cases, the cleavage region contains a disulfide linker. In some cases, cleavage region contains a 5' thiol modified uracil (e.g., 5'-thiol (thiohexyl; C6 modified). In some cases, the cleavage region is at or near the 5' end of the oligonucleotide. For example, the oligonucleotide can be conjugated to the solid support at the 5' end of the oligonucleotide and the cleavage region at or near the 5' end can enable cleavage of the oligonucleotide from the solid support. In other cases, the cleavage region is at or near the 3' end. For example, the oligonucleotide can be conjugated to the solid support at the 3' end and the cleavage region at or near the 3' end can enable cleavage of the oligonucleotide from the solid support.

In some cases, the first defined region is a capture region. The capture region of the barcoded particle, dual barcoded particle, or set of particles can be any sequence that is capable of capturing (e.g., hybridizing to) a target nucleic acid or a plurality of target nucleic acids of interest. For example, the capture region can be a poly-thymine nucleotide sequence (e.g., 10-25 or more contiguous thymine nucleotides). As another example, the capture region can hybridize to a conserved region of a gene family. As yet another example, the capture region can hybridize to a sequence containing two contiguous exons, and thus detect mature RNA expressed from a specific gene or gene family. In some cases, the capture region contains one or more inosine, nitroindole, or other universal nucleotides.

In some cases, the barcoded particle, dual barcoded particle, or set of particles, can further contain primer binding sites. For example, a T7 primer binding site or reverse complement thereof can be included for unbiased amplification of target nucleic acid. As another example, particles can include one or more sequencing primer binding sites, or the reverse complement thereof.

Solid supports suitable for barcoded or dual barcoded particles include controlled pore glass (CPG)(available from Glen Research, Sterling, Va.), oxalyl-controlled pore glass (See, e.g., Alul, et al., Nucleic Acids Research 1991, 19, 1527), TentaGel Support—an aminopolyethyleneglycol derivatized support (See, e.g., Wright, et al., Tetrahedron Letters 1993, 34, 3373), polystyrene, Poros—a copolymer of polystyrene/divinylbenzene, or reversibly cross-linked acrylamide. Many other solid supports are commercially available and amenable to the present invention.

In some cases, a plurality (e.g., at least 100; 200; 300; 500; 750; 1000; 2500; 5000; 7500; 10,000; 15,000; 20,000; 30,000; 50,000; 75,000; 100,000; 250,000; 500,000; $1 \times 10^6$ or more) of barcoded or dual barcoded particles are provided.

In some embodiments, a plurality of partitions (e.g., at least 100; 200; 300; 500; 750; 1000; 2500; 5000; 7500; 10,000; 15,000; 20,000; 30,000; 50,000; 75,000; 100,000; 250,000; 500,000; $1 \times 10^6$ or more partitions) are provided, wherein the plurality of partitions each contain a plurality of oligonucleotides, the oligonucleotides having a partition-specific barcode and a molecular barcode, wherein the partition-specific barcode is the same, or substantially the same in a partition, but unique to the plurality of partitions, and the molecular barcode is unique to the oligonucleotide molecule. In some cases, the oligonucleotides are conjugated to solid support particles, such as solid support beads. In other cases, the oligonucleotides are not conjugated. In some cases, the partitions contain a solid support particle and a plurality of oligonucleotides, wherein the plurality of oligonucleotides have been cleaved from the solid support particle.

C. Compositions for Generating Amplified Nucleic Acid or cDNA Having a Uniform Size Distribution Described herein are reagents and reagent mixtures containing a defined UTP/TTP or dUTP/dTTP ratio. In general the ratio is less than 1:1. In some cases, the ratio is about 1:2, 1/3, 1/4, 1/5, 1/6, 1/7, 1/8, 1/9, 1/10, 1/15, 1/20, 1/25, 1/30, 1/40, 1/50, 1/70, 1/75, 1/80, 1/90, 1/100, or less. In some cases, the ratio is 1:2, 1/3, 1/4, 1/5, 1/6, 1/7, 1/8, 1/9, 1/10, 1/15, 1/20, 1/25, 1/30, 1/40, 1/50, 1/70, 1/75, 1/80, 1/90, or 1/100. The mixture containing UTP and TTP, or dUTP and dTTP at a defined ratio can be used during reverse transcription and/or amplification of target nucleic acid. Thus, the U and T are incorporated into the polymerized nucleic acid at a defined ratio. Accordingly, the reagent mixture can further contain polymerase, buffers, salts, primers (e.g., barcoded primers), and other nucleotides.

The polymerized (e.g., amplified, reverse transcribed, etc.) nucleic acid can then be treated with UDG/ApeI to generate fragments of nucleic acid having a uniform size distribution. This fragmentation can be performed in manner that is not substantially time dependent. For example, unlike other enzymatic or physical fragmentation methods, the fragmentation does not generate ever smaller fragments as the treatment step is continued. Rather, assuming the reaction is performed for a sufficient amount of time and with a sufficient amount of UDG/ApeI, the size distribution of fragments is determined by the ratio of U to T. The higher the concentration of U relative to T, the more uracil nucleotides are incorporated into the polymerized strand. The more uracil nucleotides incorporated, the greater the fragmentation.

Accordingly, also described herein are reaction mixtures containing barcoded (e.g., cellular and/or molecular barcoded) deoxyribonucleic acid (DNA) (e.g., amplified, and/or reverse transcribed), wherein the DNA contains uracil nucleotides in the place of thymine nucleotides at a defined ratio of U to T. In some cases, the ratio is about 1:2, 1/3, 1/4, 1/5, 1/6, 1/7, 1/8, 1/9, 1/10, 1/15, 1/20, 1/25, 1/30, 1/40, 1/50, 1/70, 1/75, 1/80, 1/90, 1/100, or less. In some cases, the ratio is 1:2, 1/3, 1/4, 1/5, 1/6, 1/7, 1/8, 1/9, 1/10, 1/15, 1/20, 1/25, 1/30, 1/40, 1/50, 1/70, 1/75, 1/80, 1/90, or 1/100. The reaction mixture can further contain UDG/ApeI. In some cases, the reaction mixtures are in droplets or other partitions. In some cases, the reaction mixtures further contain terminal transferase.

Also described herein are reaction mixtures containing target barcoded (e.g., particle and/or molecularly barcoded) deoxyribonucleic acid (DNA). The target barcoded DNA can be, e.g., amplified, and/or reverse transcribed from RNA such as mRNA. The target barcoded DNA can be free of uracil nucleotides. and has a uniform size distribution. The DNA can be barcoded by polymerization from or ligation of a barcoded oligonucleotide to attach the barcode to the target DNA. The barcoded oligonucleotide can contain a particle and/or molecularly barcoded region, optionally a capture region for hybridizing to the DNA substrate, and a defined sequence (e.g., universal primer binding site). This barcoded target DNA can be amplified with a population of oligonucleotides that hybridize to the target barcoded DNA substrate such that the distance between hybridized primers is a uniform size distribution. The distance between adjacent oligonucleotide priming sites can be, e.g., on average, about 25, 50, 100, 200, 300, 400, 500, 600, 700, 800, 900, 1000 nucleotides, or more apart. Polymerization of the oligonucleotide primers hybridized to the barcoded target DNA can provide a plurality of polymerization products having a uniform size distribution. In some cases, the reaction mixtures are in droplets or other partitions.

III. Methods

Methods of making a plurality of partitions, each partition having a unique barcode sequence are provided. Methods of making a plurality of particles, each particle having a unique bifunctional barcode are also provided. The methods include those requiring hydrogel and those that do not rely on the use of hydrogel.

A. Methods of Making Hydrogel Particles or Partitions Having a Unique Barcode

In some embodiments, the methods for making particles or partitions having a unique partition-specific, particle, or cellular barcode in each partition include: mixing sol hydrogel and an oligonucleotide conjugate in the presence of (i) labeled reverse primer; (ii) DNA amplification reagents; and (iii) a bifunctional barcode template nucleic acid (e.g., a single-stranded bifunctional barcode template nucleic acid) having a barcode region, a first end containing a forward primer binding site and a second end containing a reverse primer binding site, to form a mixture; and then partitioning the mixture. In some cases, the oligonucleotide conjugate is a linear polyacrylamide oligonucleotide conjugate. In some cases, the oligonucleotide conjugate is directly conjugated to the hydrogel. In some cases, the bifunctional barcode template is present in the mixture at a concentration such that at least about 90%, 95%, 99.5%, or more of the plurality of partitions contain no more than 1 unique barcode molecule.

In some cases, the method further includes performing DNA amplification in the partitions to amplify the bifunctional barcode template nucleic acid and thereby covalently link the bifunctional barcode template nucleic acid to the oligonucleotide conjugate. In some cases, the DNA amplification is amplification with a forward primer encoded by the oligonucleotide conjugate and/or the labeled reverse primer. In some cases, the amplification is PCR amplification. In some cases, the amplification generates a double stranded bifunctional barcode template nucleic acid.

In some cases, the labeled reverse primer contains a capture region, which capture region is linked to the hydrogel during a polymerization and/or amplification step. The capture region can be any sequence in which the reverse complement thereof is capable of capturing (e.g., hybridizing to) a target nucleic acid or a plurality of target nucleic acids of interest. For example, the capture region can be a poly-adenine nucleotide sequence (e.g., 10-25 or more contiguous adenine nucleotides). As another example, the reverse complement of the capture region can hybridize to a conserved region of a gene family. As yet another example, the reverse complement of the capture region can hybridize to a sequence containing two contiguous exons, and thus detect mature RNA expressed from a specific gene or gene family. In some cases, the capture region of the reverse primer contains one or more inosine, nitroindole, or other universal nucleotides.

In some cases, the capture region is a randomer (e.g., a random pentamer, hexamer, septamer, or octamer). A barcoded particle having a randomer capture region can be used to hybridize to, barcode, amplify, and/or sequence target DNA having a sequence that is not pre-determined. In some cases, the randomer can be used to hybridize to, barcode, amplify, and/or sequence long fragment DNA targets. For example, the randomer can hybridize to a plurality of positions on a long fragment DNA target and produce a plurality of barcoded sub-fragments for subsequent analysis. The barcoded sub-fragments (e.g., sub-fragments in a single partition) can contain a shared long DNA fragment barcode and/or a unique molecular barcode.

In some cases, the method further includes hardening the sol hydrogel to a gel form to generate a plurality of labeled hydrogel particles, each particle in a partition, and each particle comprising an oligonucleotide conjugate, wherein the oligonucleotide conjugate is covalently linked to the bifunctional barcode template nucleic acid, and wherein each labeled hydrogel particle contains a unique barcode sequence. In some cases, each particle can further contain a plurality of molecular barcode sequences. In some cases, the partitions can be combined to obtain a set of labeled hydrogel particles each containing a unique barcode sequence.

Hydrogel particles described herein (e.g., particles containing a molecular and/or cellular/particle barcode) can comprise a large number of oligonucleotides. Typically, 1,000; 10,000; 100,000; $1\times10^6$; $1\times10^7$, or more oligonucleotides are attached to a particle.

In some embodiments, labeled hydrogel particles can be separated from unlabeled hydrogel particles using, e.g., a solid support-bound affinity agent having affinity for the label. For example, the affinity agent can be contacted with the particles and unlabeled, and therefore unbound, hydrogel particles removed by washing the solid support.

In some embodiments, labeled hydrogel particles having double stranded nucleic acid containing a unique barcode and a capture region, and optionally molecular barcodes, can then be further treated to generate hydrogel particles having single stranded nucleic acid containing a unique barcode and a capture region, and optionally molecular barcodes. For example, in some cases, a labeled hydrogel particle or set of labeled hydrogel particles each containing a unique barcode sequence is treated to remove the label, remove the labeled reverse primer, and/or remove the labeled single or double-stranded product generated by polymerization or amplification from the labeled reverse primer. In some cases, the labeled hydrogel particles can be captured with the affinity agent having affinity for the label, and the particles then subject to nucleic acid denaturation conditions. Exemplary nucleic acid denaturation conditions include heat or alkaline denaturation, or a combination thereof. In some cases, alkaline denaturation is performed by contacting the labeled hydrogel particle or particles with an alkaline hydroxide or other base. The hydrogel particle or set of particles can then be recovered while the label remains bound to the affinity agent.

In some embodiments, the hydrogel particles, each having a unique barcode, are partitioned into a plurality of partitions. In some cases, the hydrogel particles each have a unique barcode and a plurality of molecular barcodes. In some cases, the partitioning is performed under conditions such that all, substantially all, or a majority of the partitions contain no more than 1 hydrogel particle. In some cases, the partitioning is performed under conditions such that each partition, substantially all partitions, or a majority of partitions contain a hydrogel particle. In some cases, partitions that do not contain a hydrogel particle are separated from partitions that contain a hydrogel particle. For example, partitions lacking a hydrogel particle can be removed by optical sorting (e.g., fluorescence activated particle sorting), volume based sorting (e.g., using the Coulter principle), or density based sorting (e.g., centrifugation).

In some cases, the hydrogel particles are partitioned in the presence of a plurality of cells, such that each partition contains a hydrogel particle and a single cell, or nucleic acid from a single cell. For example, hydrogel particles can be partitioned in the presence of a plurality of cells, such that each partition contains a hydrogel particle and a single cell, and then the cells can be lysed. In some cases, the hydrogels are partitioned in the presence of a plurality of cells and in the presence of a cell lysis reagent (e.g., detergent), such that upon partitioning, the cells lyse in the partitions. In some cases, the partitions are treated (e.g., heated) to lyse partitioned cells therein.

Alternatively, a plurality of partitions each with a single cell can be formed, the cells optionally lysed, and barcoded particles then incorporated into the plurality of partitions. As yet another alternative, a plurality of partitions each with a barcoded hydrogel can be formed and cells incorporated therein. As yet another alternative, a plurality of partitions, each with a barcoded hydrogel, and a plurality of partitions, each containing a single cell or nucleic acid from a single cell, can be formed. The hydrogel containing partitions can then be combined with the single cell/nucleic acid containing partitions to form a plurality of partitions containing a barcoded hydrogel and a single cell or nucleic acid from a single cell.

In some embodiments, the partitions are formed in the presence of template directed nucleic acid polymerization reagents. Exemplary template directed nucleic acid polymerization reagents include polymerases (e.g., thermostable DNA polymerase, or reverse transcriptase), nucleotides, buffers, salts, oligonucleotide primers etc. Template directed nucleic acid polymerization reagents further include reagents for performing reverse transcription.

In some embodiments, partitions containing a single cell, or partitions containing a hydrogel particle and a single cell are lysed. Cells can be lysed by methods commonly known in the art. Exemplary methods for lysing cells include heating the partitions or incorporating detergent into the partitions. In some cases, cells are lysed during DNA amplification (e.g., during thermocycling) and/or reverse transcription.

Additional compositions and methods for making and using hydrogels, such as barcoded hydrogels, include those described in, e.g., Klein et al., Cell. 2015 May 21; 161(5): 1187-201.

B. Methods of Making Particles or Partitions Having a Unique Barcode that do not Require Hydrogel Particles having a unique particle or cellular barcode that do not require hydrogel can be synthesized. In some cases, the particles can be synthesized in a standard oligonucleotide synthesizer. Alternatively, the synthesis can be performed manually. Oligonucleotide synthesis can be performed from 3' to 5', or from 5' to 3' using methods known in the art. Methods for synthesizing oligonucleotides include conversion to the phosphoramidite followed by solid phase chemistries. Representative solid phase techniques are those typically employed for DNA and RNA synthesis utilizing standard phosphoramidite chemistry. (See, e.g., Protocols For Oligonucleotides And Analogs, Agrawal, S., ed., Humana Press, Totowa, N. J., 1993.). Equipment for such synthesis is sold by several vendors including Applied Biosystems.

Any suitable particle for performing solid phase oligonucleotide synthesis can be utilized. Solid supports suitable for barcoded or particles include controlled pore glass (CPG)(available from Glen Research, Sterling, Va.), oxalyl-controlled pore glass (See, e.g., Alul, et al., Nucleic Acids Research 1991, 19, 1527), TentaGel Support—an aminopolyethyleneglycol derivatized support (See, e.g., Wright, et al., Tetrahedron Letters 1993, 34, 3373) or Poros—a copolymer of polystyrene/divinylbenzene. Many other solid supports are commercially available and amenable to the present invention.

In some embodiments, the particles are synthesized using a split, conjugate, and mix method to generate a particle barcode. In some cases, the split and mix method can be performed by providing a plurality of particles for performing solid phase oligonucleotide synthesis. In some cases, the particles are provided with oligonucleotides conjugated thereon. For example, the particles can have a first defined or a second defined region conjugated thereon prior to performing the split, conjugate, and mix method for generating a particle barcode. In some cases, the particles can have a molecular barcode conjugated thereon prior to performing the split, conjugate, and mix method for generating a particle barcode.

The provided particles can be split into four different reaction mixtures, each reaction mixture conjugating a different nucleotide to the particles. For example, a first reaction mixture conjugates adenine, a second reaction mixture conjugates guanine, a third reaction mixture conjugates cytosine, and a fourth reaction mixture conjugates thymine. After conjugation is completed, the products from the four different reaction mixtures are then combined, mixed, and split into four different reaction mixtures, each reaction mixture conjugating a different nucleotide to the particles. The splitting, conjugating, and mixing can repeated to produce an arbitrarily long unique barcode for each particle. Typically, the number of repeats is selected so that the length of the particle barcodes, and thus the number of possible particle barcode sequences, greatly exceeds (e.g., at least 2-fold, 10-fold, 100-fold, or more) the number of particles. For example, if the number of particles is $10^3$, then a barcode containing at least 100,000 possible sequences can be generated by repeating the splitting, conjugating, and mixing at least 9 times to produce a barcode containing $4^9$ (=262,144) possible sequences.

In some cases, the splitting, conjugating, and mixing is repeated from about 1 to about 50 times, from about 2 to about 20 times, from about 5 to about 20 times, from about 6 to about 20 times, from about 7 to about 20 times, from about 8 to about 20 times, from about 9 to about 20 times, from about 10 to about 20 times, 10 to 14 times, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 times.

In some embodiments, the particles are subject to degenerate nucleotide synthesis to generate molecular barcodes. For example, an equimolar, or equikinetic, mixture of nucleotides can be conjugated to a plurality of particles. The conjugation can be repeated to produce an arbitrarily long unique barcode for each oligonucleotide molecule. Typically, the number of repeats is selected so that the length of the molecular barcodes, and thus the number of possible molecular barcode sequences, greatly exceeds (e.g., at least 2-fold, 10-fold, 100-fold, or more) the number of oligonucleotides. For example, if a particle is expected to contain approximately $10^6$ oligonucleotides, then the degenerate nucleotide conjugation step can be repeated at least 10 times to produce molecular barcodes containing $4^{12}$ (=16,777,216) possible sequences.

In some cases, the conjugation of a degenerate mixture of nucleotides is repeated from about 5 to about 50 times, from about 6 to about 20 times, from about 7 to about 20 times, from about 8 to about 20 times, from about 9 to about 20 times, from about 10 to about 20 times, from about 11 to about 20 times, from about 12 to about 20 times, 10 to 14 times, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 times.

In some embodiments, barcoded particles or dual barcoded particles are further conjugated to a first and/or a second defined region. The first region can contain a capture region that hybridizes to a target nucleic acid. In some cases, the first region can contain a cleavage region. The second region can contain a defined region for downstream processing. For example, the second region can contain a defined sequence for primer binding for amplification, and/or sequencing (e.g., a universal primer binding site). As another example, the second region can contain a defined sequence suitable for ligation to one or more target polynucleotides. As another example, the first region can contain a defined sequence suitable for ligation to one more target polynucleotides. As another example the defined sequence of the first or second capture region can become suitable for ligation upon oligonucleotide processing (e.g., cleavage, uracil excision, primer binding, polymerization, addition of nucleotides by terminal transferase, phosphorylation, dephosphorylation, etc.). Oligonucleotide processing may include, e.g., oligonucleotide cleavage, uracil excision, primer binding, polymerization, addition of nucleotides by terminal transferase, phosphorylation, dephosphorylation, etc. Primer binding may include annealing of one or more oligonucleotides containing one or more modified nucleotides, e.g., containing one or more uracil nucleotides, or containing modified 5' hydroxyl termini.

The capture region can be any sequence that is capable of capturing (e.g., hybridizing to) a target nucleic acid or a plurality of target nucleic acids of interest. For example, the capture region can be a poly-thymine nucleotide sequence (e.g., 10-25 or more contiguous thymine nucleotides). As another example, the capture region can hybridize to a conserved region of a gene family. As yet another example, the capture region can hybridize to a sequence containing two contiguous exons, and thus detect mature RNA expressed from a specific gene or gene family. In some cases, the capture region contains one or more inosine, nitroindole, or other universal nucleotides.

In some cases, the capture region is a randomer (e.g., a random pentamer, hexamer, septamer, or octamer). A barcoded particle having a randomer capture region can be used to hybridize to, barcode, amplify, and/or sequence target DNA having a sequence that is not pre-determined. In some cases, the randomer can be used to hybridize to, barcode, amplify, and/or sequence long fragment DNA targets. For example, the randomer can hybridize to a plurality of positions on a long fragment DNA target and produce a plurality of barcoded sub-fragments for subsequent analysis. The barcoded sub-fragments (e.g., sub-fragments in a single partition) can contain a shared long DNA fragment barcode and/or a unique molecular barcode.

Non-hydrogel oligonucleotide particles described herein, including, but not limited to, non-hydrogel particles made by solid phase synthesis of oligonucleotides onto the particles (e.g., containing a molecular and/or cellular/particle barcode) can comprise a large number of oligonucleotides. Typically, 1,000; 10,000; 100,000; $1\times10^6$; $1\times10^7$, or more oligonucleotides are attached to such a particle.

Additional compositions and methods for making and using non-hydrogel particles, such as barcoded particles, include those described in, e.g., Macosko et al., Cell. 2015 May 21; 161(5):1202-14.

C. Methods of Performing Single Cell Analysis

In some embodiments, a method for single cell analysis is provided. For example, a partition can be provided, wherein the partition contains a unique partition-specific barcode oligonucleotide having a barcode and a capture region, a single cell or nucleic acid from a single cell, and reagents for template directed nucleic acid polymerization. The capture region of the barcode oligonucleotide can be configured to hybridize to one or more target nucleic acids as described herein. The barcode oligonucleotide can further contain a molecular barcode, wherein the molecular barcode is unique for every barcode oligonucleotide molecule in the partition or in each partition of the set of partitions. In some embodiments, the barcode oligonucleotide is conjugated to a hydrogel. In some embodiments, the barcode oligonucleotide is conjugated to a high molecular weight polymer and the partition further contains hydrogel. In some embodiments, the barcode oligonucleotide is conjugated to a solid support. In some embodiments, the barcode oligonucleotide is not conjugated to a hydrogel, high molecular weight polymer, or a solid support.

In some embodiments, a high throughput method for single cell analysis is provided. For example, a set of partitions can be provided, wherein the set of partitions (e.g., at least 100; 200; 300; 500; 750; 1000; 2500; 5000; 7500; 10,000; 15,000; 20,000; 30,000; 50,000; 75,000; 100,000; 250,000; 500,000; or $1\times10^6$ partitions) each contain a barcode oligonucleotide having a unique partition-specific barcode and a capture region, a single cell or nucleic acid from a single cell, and reagents for performing template directed nucleic acid polymerization.

In some cases, the partition or set of partitions contain hydrogel (e.g., in sol or gel form). For example, partition or the set of partitions can contain a bifunctional barcode conjugated to hydrogel, the bifunctional barcode having a barcode region and a capture region. In some cases, the bifunctional barcode can have multiple barcode regions, such as a molecular barcode region and a particle barcode region. In some cases, the set of partitions can contain a bifunctional barcode conjugated to a high molecular weight polymer such as linear polyacrylamide. In some cases, the bifunctional barcode conjugated to a high molecular weight polymer is encapsulated in a gel form hydrogel matrix. In some cases, the partition or partitions each contain a gel form hydrogel and a single cell, and the hydrogel is converted to a sol form, e.g., by heating. In some cases, after converting the hydrogel to the sol form, the sol hydrogel is diluted in the partition such that it does not form a gel form at room temperature.

In some embodiments, the partition or set of partitions contains oligonucleotides (e.g., partition-specific and/or molecular barcode oligonucleotides) attached to a solid support. In some embodiments, the oligonucleotides attached to a solid support are cleaved from the solid support in the partition or after partitions are subsequently combined (e.g., after ligation, hybridization, polymerization, and/or amplification in the partitions followed by combining of partitions). Methods of cleaving include, but are not limited to altering the pH or contacting the oligonucleotides with UDG/ApeI or a restriction endonuclease. In some cases, the oligonucleotides are attached to a solid support through a disulfide linkage (e.g., through a disulfide bond between a sulfide of the solid support and a sulfide covalently attached to the 5' or 3' end, or an intervening nucleic acid, of the oligonucleotide). In such cases, the oligonucleotide can be cleaved from the solid support by contacting the solid support with a reducing agent such as a thiol or phosphine reagent, including but not limited to a beta mercaptoethanol, dithiothreitol (DTT), or tris(2-carboxyethyl)phosphine (TCEP).

In some embodiments, the partition, or set of partitions, contains a single cell, or the set of partitions each contain a single cell. The cell(s) can be lysed using any method known in the art, including but not limited to heating or contacting with detergent. After lysis, the partition, or set of partitions, contains nucleic acid from a single cell.

Nucleic acid from a single cell in the partition, or in each of the partitions in a set of partitions, can be barcoded by performing template directed nucleic acid polymerization in the partition, wherein the polymerization is primed by the capture region of the barcoded oligonucleotide. For example, the capture region can hybridize to target nucleic acid(s) in the cell, and polymerization performed. In some cases, the capture region comprises a poly-thymine sequence and hybridizes to mRNA of the cell. In such cases, polymerization can comprise reverse transcription. Additionally, or in the alternative, polymerization can comprise amplification of RNA, mRNA, microRNA, DNA, or cDNA.

Polymerization primed by the capture region of the barcoded oligonucleotide can thereby barcode the nucleic acid of the cell or polymerization products thereof (e.g., amplicons, cDNA, etc.). The barcoded nucleic acid can thereby contain a barcode that uniquely identifies the single cell from which it derives. In some cases, the barcode oligonucleotide further contains a molecular barcode and the barcoded nucleic acid thereby also contains a barcode that uniquely identifies the nucleic acid molecule from which it derives. After the nucleic acid is barcoded, the nucleic acid can be recovered from the partition or set of partitions for downstream processing. For example, sequencing (e.g., high throughput sequencing) can be performed on the barcoded nucleic acid. Additionally or alternatively, genotyping can be performed on the barcoded nucleic acid.

In some embodiments, the library of barcoded nucleic acids can be fragmented to obtain nucleic acid products of a desired size or size distribution. Methods of fragmentation are known in the art and include physical methods such as sonication or shearing, chemical methods, and enzymatic methods (e.g., DNaseI). In some cases, the barcoded nucleic acids can be generated in the presence of UTP and TTP or dUTP and dTTP at a defined ratio, thereby incorporating uracil into the place of thymine at that defined ratio. In some cases, the ratio of U to T is about 1:2, 1/3, 1/4, 1/5, 1/6, 1/7, 1/8, 1/9, 1/10, 1/15, 1/20, 1/25, 1/30, 1/40, 1/50, 1/70, 1/75, 1/80, 1/90, 1/100, or less. In some cases, the ratio is 1:2, 1/3, 1/4, 1/5, 1/6, 1/7, 1/8, 1/9, 1/10, 1/15, 1/20, 1/25, 1/30, 1/40, 1/50, 1/70, 1/75, 1/80, 1/90, or 1/100. In such cases, the nucleic acids can be fragmented by contacting with UDG/ApeI.

Fragmented barcoded nucleic acid can be hybridized to one or more additional primers to add adaptor sequences and amplified. In some cases, the fragmented barcoded nucleic acids are contacted with a terminal transferase to add a polynucleotide (e.g., poly-A, poly-T, poly-G, or poly-C) to generate one or more adaptor primer binding sites. Alternatively, the fragmented barcoded nucleic acid can be ligated to one or more adaptor oligonucleotides. The adaptors can contain sequencing primer binding sites and other sequences useful for quantitation and/or high throughput sequencing.

Methods for high throughput sequencing and genotyping are known in the art. For example, such sequencing technologies include, but are not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety).

Exemplary DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the present technology provides parallel sequencing of partitioned amplicons (PCT Publication No. WO 2006/0841,32, herein incorporated by reference in its entirety). In some embodiments, DNA sequencing is achieved by parallel oligonucleotide extension (See, e.g., U.S. Pat. Nos. 5,750,341; and 6,306,597, both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; and U.S. Pat. Nos. 6,432,360; 6,485,944; 6,511,803; herein incorporated by reference in their entireties), the 454 picotiter pyrosequencing technology (Margulies et al., 2005 Nature 437, 376-380; U.S. Publication No. 2005/0130173; herein incorporated by reference in their entireties), the Solexa single base addition technology (Bennett et al., 2005, Pharmacogenomics, 6, 373-382; U.S. Pat. Nos. 6,787,308; and 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 2000/018957; herein incorporated by reference in its entirety).

Typically, high throughput sequencing methods share the common feature of massively parallel, high-throughput strategies, with the goal of lower costs in comparison to older sequencing methods (See, e.g., Voelkerding et al., Clinical Chem., 55: 641-658, 2009; MacLean et al., Nature Rev. Microbiol., 7:287-296; each herein incorporated by reference in their entirety). Such methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbial., 7:287-296; U.S. Pat. Nos. 6,210,891; and 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55. 641-658, 2009; MacLean et al., Nature Rev. Microbial., 7:287-296; U.S. Pat. Nos. 6,833,246; 7,115,400; and 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbial., 7:287-296; U.S. Pat. Nos. 5,912,148; and 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing is employed (See, e.g., Astier et al., J. Am. Chem. Soc. 2006 Feb. 8; 128(5)1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HeliScope by Helicos BioSciences is employed (Voelkerding et al., *Clinical Chem.,* 55. 641-658, 2009; MacLean et al., *Nature Rev. Microbial,* 7:287-296; U.S. Pat. Nos. 7,169,560; 7,282,337; 7,482,120; 7,501,245; 6,818,395; 6,911,345; and 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (See, e.g., Science 327 (5970): 1190 (2010); U.S. Pat. Appl. Pub. Nos. 2009/0026082; 2009/0127589; 2010/0301398; 2010/0197507; 2010/0188073; and 2010/0137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers the hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

Another exemplary nucleic acid sequencing approach that may be adapted for use with the present invention was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 2009/0035777, which is incorporated herein in its entirety.

Other single molecule sequencing methods include real-time sequencing by synthesis using a VisiGen platform (Voelkerding et al., Clinical Chem., 55: 641-58, 2009; U.S. Pat. No. 7,329,492; and U.S. patent application Ser. Nos. 11/671,956; and 11/781,166; each herein incorporated by reference in their entirety) in which immobilized, primed DNA template is subjected to strand extension using a fluorescently-modified polymerase and florescent acceptor molecules, resulting in detectable fluorescence resonance energy transfer (FRET) upon nucleotide addition.

Another real-time single molecule sequencing system developed by Pacific Biosciences (Voelkerding et al., Clinical Chem., 55. 641-658, 2009; MacLean et al., Nature Rev. Microbiol., 7:287-296; U.S. Pat. Nos. 7,170,050; 7,302,146; 7,313,308; and 7,476,503; all of which are herein incorporated by reference) utilizes reaction wells 50-100 nm in diameter and encompassing a reaction volume of approximately 20 zeptoliters ($10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Processes and systems for such real time sequencing that may be adapted for use with the invention are described in, for example, U.S. Pat. Nos. 7,405,281; 7,315,019; 7,313,308; 7,302,146; and 7,170,050; and U.S. Pat. Pub. Nos. 2008/0212960; 2008/0206764; 2008/0199932; 2008/0199874; 2008/0176769; 2008/0176316; 2008/0176241; 2008/0165346; 2008/0160531; 2008/0157005; 2008/0153100; 2008/0153095; 2008/0152281; 2008/0152280; 2008/0145278; 2008/0128627; 2008/0108082; 2008/0095488; 2008/0080059; 2008/0050747; 2008/0032301; 2008/0030628; 2008/0009007; 2007/0238679; 2007/0231804; 2007/0206187; 2007/0196846; 2007/0188750; 2007/0161017; 2007/0141598; 2007/0134128; 2007/0128133; 2007/0077564; 2007/0072196; and 2007/0036511; and Korlach et al. (2008) "Selective aluminum passivation for targeted immobilization of single DNA polymerase molecules in zero-mode waveguide nanostructures" PNAS 105(4): 1176-81, all of which are herein incorporated by reference in their entireties.

IV. Kits

Kits are provided for analyzing the nucleic acid of a single cell. In some embodiments, the kit can contain a plurality of barcoded particles, each particle having a unique barcode and a capture region. In some cases, the particles contain, or consist of, hydrogel (e.g., a reversible hydrogel such as agarose). The particles can further comprise molecular barcodes, wherein the molecular barcodes are unique for every oligonucleotide on a particle or unique for every oligonucleotide on the plurality of particles.

In some cases, the kits contain reagents for partitioning the plurality of particles into a plurality of partitions. In some cases, the reagents for partitioning include a water immiscible liquid for forming emulsion droplets. In some cases, the reagents include an apparatus containing a plurality of microchannels, or a plurality of micro- or nanowells.

All patents, patent applications, and other publications, including GenBank Accession Numbers, cited in this application are incorporated by reference in the entirety for all purposes.

V. Examples

The following examples are provided by way of illustration only and not by way of limitation. A variety of non-critical parameters can be changed or modified to yield essentially the same or similar results.

Example 1

Hydrogel Based Barcode Process, and Overview

An overview of the hydrogel based barcode process is provided in FIG. 1. In brief, bifunctional barcode oligonucleotides having a barcode and two functional ends are amplified onto a hydrogel particle by amplifying the bifunctional barcode oligonucleotide with at least one primer that is covalently coupled to the hydrogel or covalently coupled to a high molecular weight polymer that will be encapsulated by the hydrogel as it is converted to a gel form. After amplification, the polymer is hardened into a particle, resulting in a large number of hydrogel particles (e.g., >$10^6$), each with a large number (e.g., >$10^6$) of copies of a unique functional DNA barcode. FIG. 1A. The barcode library can be combined with another set of emulsion droplets, each containing an object to barcode, such as purified nucleic acids or cells. After barcoding, the drops can be pooled and subjected to downstream processing, such as DNA sequencing. FIG. 1B.

Example 2

Hydrogel Based Barcode Process

Figure 2:
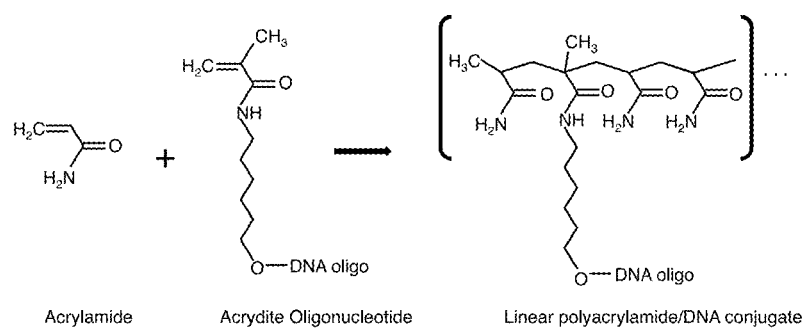
FIG. 2: Polyacrylamide-oligonucleotide synthesis. A DNA oligonucleotide is covalently attached to polyacrylamide polymer by executing the polymerization of acrylamide in the presence of a DNA oligonucleotide that has been synthesized with an acyridite moiety at the 5' end. The product is high-molecular-weight linear polyacrylamide (LPA) that has DNA oligonucleotides covalently coupled along its length.

A DNA oligonucleotide having a forward primer is covalently attached to an acrydite moiety at the 5' end. A reaction mixture containing acrylamide monomer, catalyst, initiator, and acrydite-oligonucleotide is formed, thereby incorporating one or more copies of the oligonucleotide into a high molecular weight linear polyacrylamide. FIG. 2. The linear polyacrylamide oligonucleotide conjugate, sol form agarose, biotinylated reverse primer having a poly-adenine capture region, PCR reagents, and a bifunctional barcode nucleic acid template having a forward and reverse primer binding site and a barcode are partitioned into a plurality of droplet partitions. FIG. 3A. The partitioning is performed at a concentration of bifunctional barcode nucleic acid template such that at least 90%, 95%, 99%, substantially all, or all of the partitions do not contain more than one bifunctional barcode nucleic acid template. FIG. 3B,1.

Figure 3:
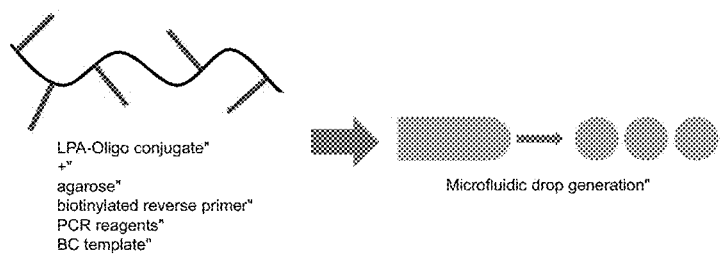
FIG. 3: Barcode particle fabrication A) LPA-oligonucleotide conjugate (forward primer) is mixed with hydrogel, biotinylated reverse primer, PCR reagents and the barcode template and this solution is incorporated into uniform water-in-oil drops using a microfluidic device. B1) The concentrations are such that the primers are at high enough concentrations to have many millions per drop, but the template is at a concentration of less than one per drop. This ensures that there is only a single template, or none, in any drop for substantially all drops. For RNA-seq applications, the template contains a T7 promoter for unbiased amplification, a sequencing primer binding site, the barcode region and the primer binding site for amplification. The reverse primer binds to the PBS and appends an "oligo dT" function that allows capture of poly-A mRNA. The reverse primer also has a 5' biotin that will allow enrichment of "PCR positive" beads later in the process. B2) The drops are thermally cycled to PCR amplify the template molecules. Drops that originally contained a template molecule now contain millions of copies of double-stranded DNA with the oligo-dT functional block and biotin appended. B3) The beads are hardened into particles and washed out of the oil into an aqueous suspension. PCR-positive beads are enriched by magnetic streptavidin particles, and the biotinylated strand is removed by alkaline denaturation and washing of the particles.
Figure 3:
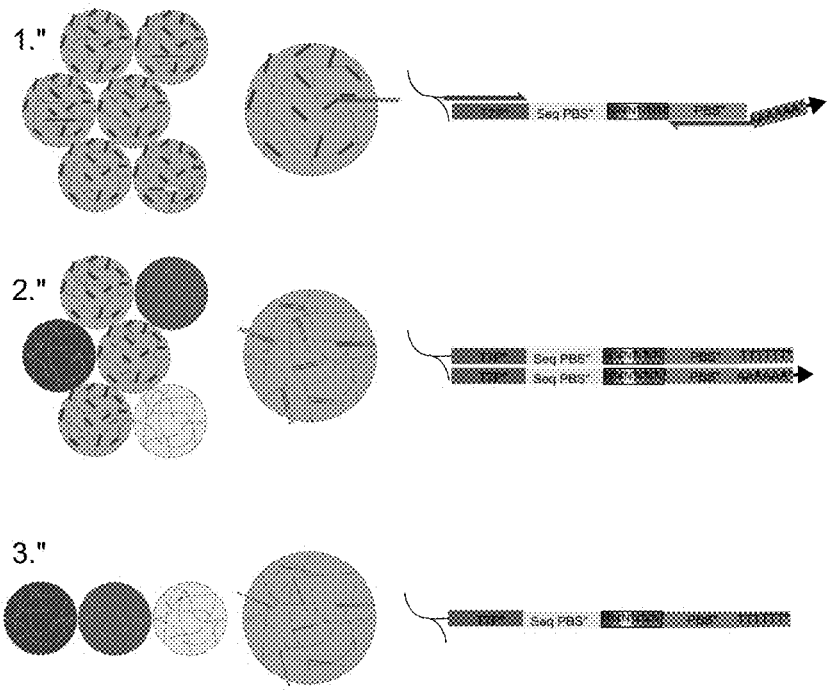

The reverse primer binds to the reverse primer binding site and appends poly-thymine function that allows capture of poly-adenine mRNA. The reverse primer also contains a 5' biotin that allows enrichment of amplified particles. FIG. 3B,2 The drops are thermally cycled to PCR amplify the bifunctional barcode template molecules. Drops that originally contained a template molecule now contain millions of copies of double-stranded DNA with a poly-thymine capture region and biotin label. FIG. 3B,3. The hydrogel is converted to gel form and the particles are washed out of the emulsion into an aqueous suspension. Amplified beads are enriched by contacting with magnetic streptavidin particles, and the biotinylated strand is removed by washing of the particles under alkaline denaturation conditions to thereby generate a library of barcoded hydrogel particles.

Figure 4:
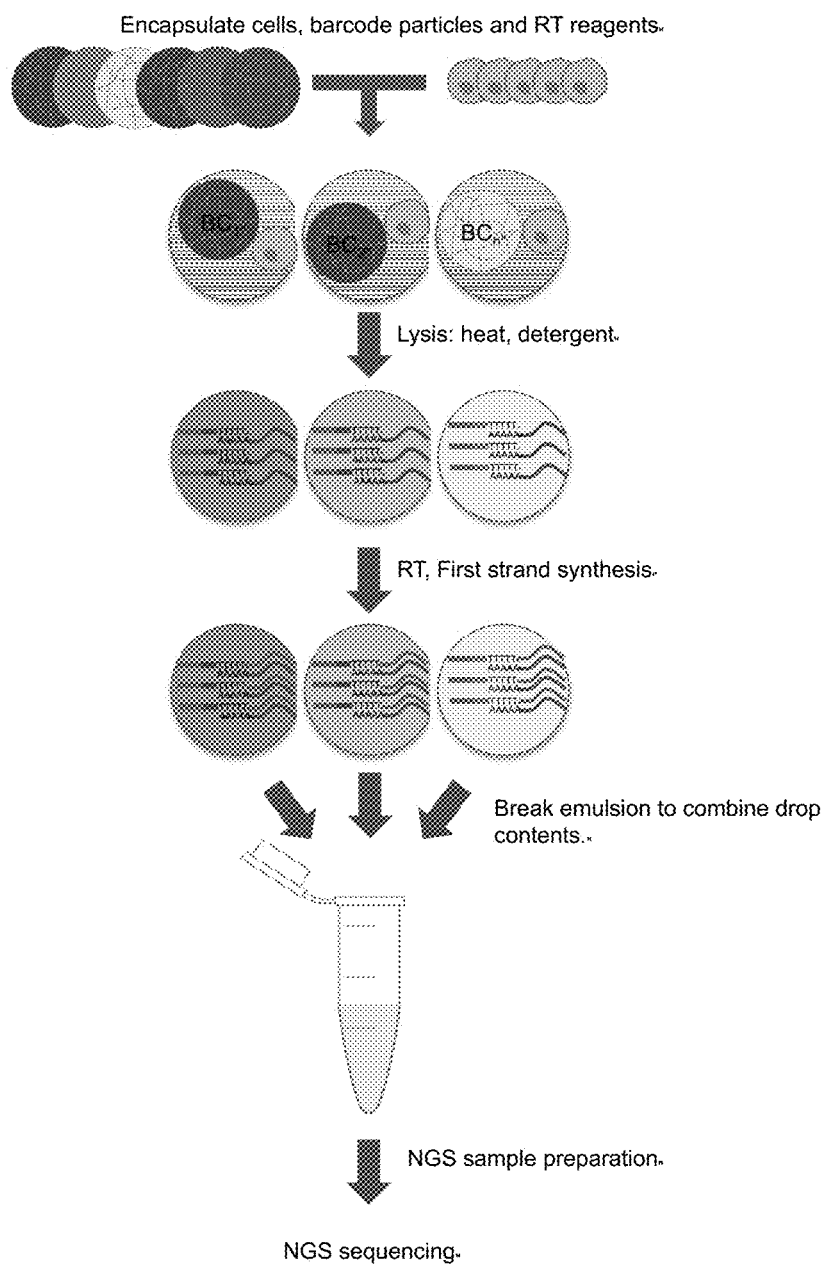
FIG. 4: Single cell RNA barcoding for single-cell expression profiling (RNA-Seq). A library of barcode gel particles is mixed with a multitude of cells in a microfluidic device, and co-encapsulated into an aqueous droplet containing reagents to lyse the cell and perform reverse transcription on the RNA. The drops are heated to melt the agarose gel and lyse the cell, thereby allowing contact between the cellular RNA and the barcode oligonucleotides. The drops are cooled to a temperature that allows the reverse transcriptase enzyme to act, and first-strand synthesis (FSS) occurs within the drop. The FSS reaction appends a barcode to every transcript that is reverse transcribed. The emulsion is broken, thereby pooling all the FSS reactions into a single tube. Since the RNA is already barcoded, the rest of the library preparation for sequencing occurs with the pooled drops in a single tube. Finally, the prepared library is sequenced by NGS. Deconvolution of the barcodes allows the reads from each cell to be uniquely identified.

A library of barcoded hydrogel particles is mixed with a sample of cells in a microfluidic device and co-encapsulated into an aqueous droplet containing reagents to lyse the cell and perform reverse transcription of the RNA of the cell. The encapsulation is performed under conditions such that at least 50%, 60%, 75%, 80%, 85%, 90%, 95%, or more of the droplets contain no more than one cell. Alternatively, the encapsulation is performed under conditions such that at least 50%, 60%, 75%, 80%, 85%, 90%, 95%, or more of the droplets contain a single cell. The droplets are heated to melt the hydrogel and lyse the cell, thereby allowing contact between the cellular RNA and the barcoded oligonucleotides. The droplets are cooled to a temperature to allow reverse transcriptase activity, thereby performing first strand synthesis in the droplet. The first strand synthesis appends a cellular barcode to every transcript that is reverse transcribed in the droplet. The emulsion is broken, thereby pooling all the first strand synthesis reactions into a single tube. Since the RNA is already barcoded, the remaining sequencing steps can be performed without maintaining physical partitioning. The prepared library is sequenced by high throughput sequencing, and deconvolution of the cellular barcodes allows sequence information from each cell to be uniquely identified. FIG. 4.

Example 3

Split and Mix Barcode Process

Figure 5:
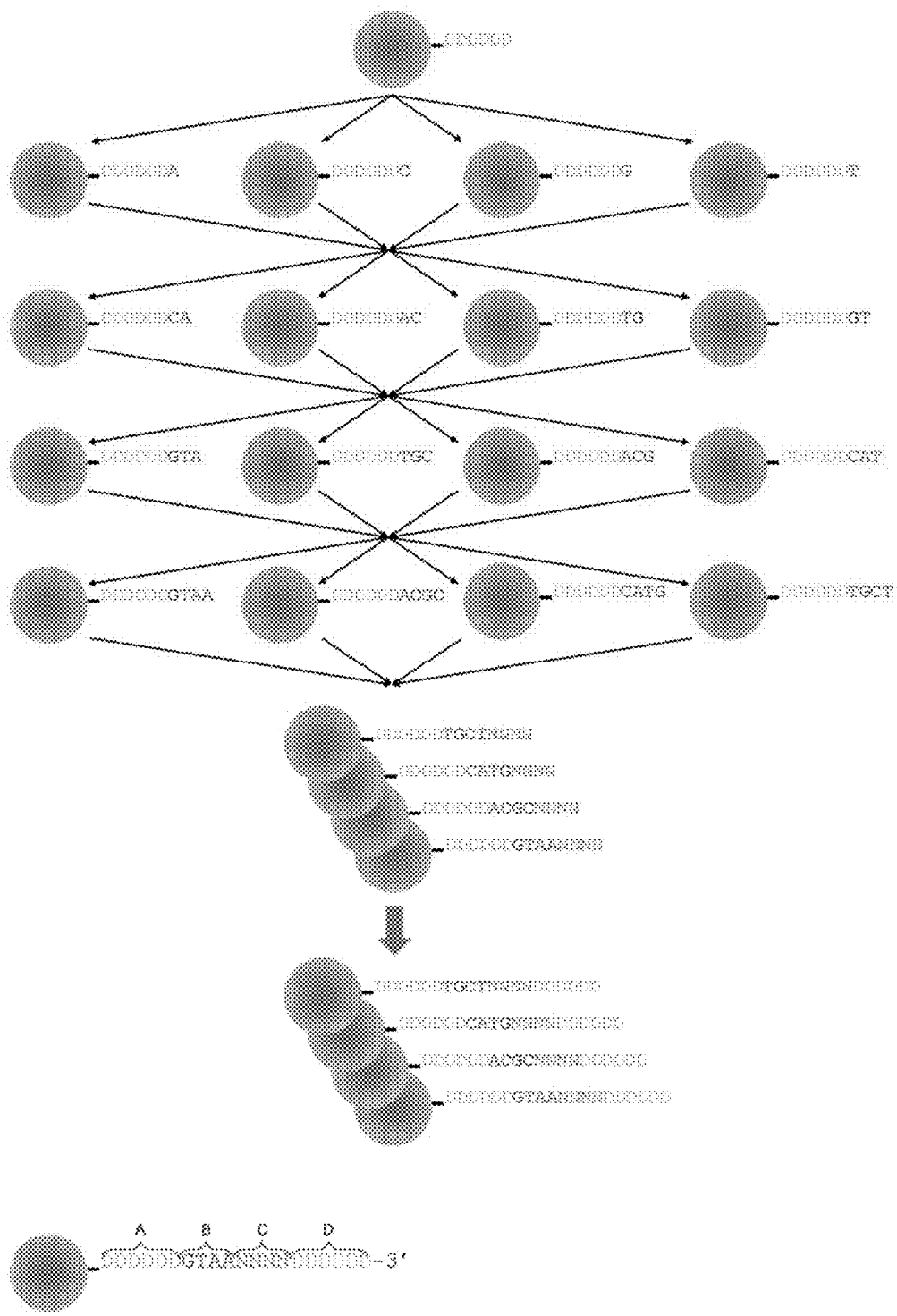
FIG. 5: Direct synthesis of barcode library onto beads. 1) DNA is synthesized on beads from a DNA synthesis resin, such as 30 μm diameter polystyrene particles. The first nucleotides added are a defined sequence (D=defined). In the case of the RNA-seq application, these would typically be 15-20 T nucleotides used to capture mRNA. 2) "split and mix" The beads are split into four separate reactions where either an A, C, G, or T nucleotide is added (SEQ ID NOS:1-4). Then the four reactions are combined, mixed and split again and another nucleotide is added. This would typically be 10-14 nucleotides added in the split-and-mix portion. At the end of this process, all the oligonucleotides on a bead are identical, and each bead is unique. This is the cell barcode. 3) The beads are recombined and several "Ns" are added (equal, or equikinetic, amounts of each nucleotide) for 10-14 cycles (SEQ ID NOS:5-8). For this N-block of nucleotides, every oligonucleotide on each bead is unique. This is the molecular barcode. Finally, another block of defined nucleotides are added, which act as a binding site for PCR or appending other functions, such as sequencing adapters (SEQ ID NOS:9-12). 5. The oligonucleotide can be synthesized from 5' to 3'. For example, 5' to 3' synthesis can be performed using reverse amidite chemistry. In such cases, the 18-25 nt defined capture sequence (SEQ ID NO:12) described herein can be free to bind target nucleic acid and prime polymerization (e.g., reverse transcription) with or without cleavage from the bead. In some cases, when the oligonucleotide is synthesized from 5' to 3', the final oligonucleotide consists of four blocks from 5'-3': A) An approximately 18-25 nt defined capture sequence, for example poly-T for capture of mRNA. There may also be a defined sequence or nucleotide analogues for cleavage of the oligonucleotide off the bead. B) A cell barcode block. Every oligonucleotide on a given bead is the same in this block, but each bead is different. C) Molecule barcode. Every oligonucleotide has a unique molecular barcode. D) A defined region for downstream amplification. All beads and oligonucleotides have the same sequence in this region. Alternatively (not depicted), the oligonucleotide can be synthesized from 3' to 5'.

DNA is synthesized from a DNA synthesis resin (e.g., 30 μm diameter polystyrene beads). The first nucleotides are added as a defined sequence. In the case of RNA-seq applications, these are 15-20, or 15-35, contiguous thymine nucleotides for capturing mRNA. FIG. 5,1. The particles are split and mixed into four separate reactions where either an A, C, G, or T nucleotide is added. Then the four reactions are combined, mixed, and split again, and another nucleotide is added. The split and mix process is repeated 10-14 times, thereby generating a unique particle barcode on each bead. FIG. 5,2. The beads are combined and conjugated to an equimolar mixture of nucleotides for 10-14 cycles. This generates a unique molecular barcode for every oligonucleotide on each particle. FIG. 5,3. Finally another block of defined nucleotides is added, which act as a binding site for PCR or appending other functions, such as sequencing adaptors. FIG. 5,4. The final oligonucleotide consists of four blocks from 3' to 5': A) ~18-25 nt defined capture sequence, for example poly-T for capture of mRNA, there may also be a defined sequence or nucleotide analogues for cleavage of the oligonucleotide off the bead; B) the cell barcode block, every oligonucleotide on a given bead is the same, but each bead is different; C) molecular barcode, every oligonucleotide is unique; and D) defined region for downstream amplification, all beads and oligonucleotides have the same sequence. FIG. 5,5.

Example 4

High-Throughput Single-Cell mRNA Analysis

Figure 6:
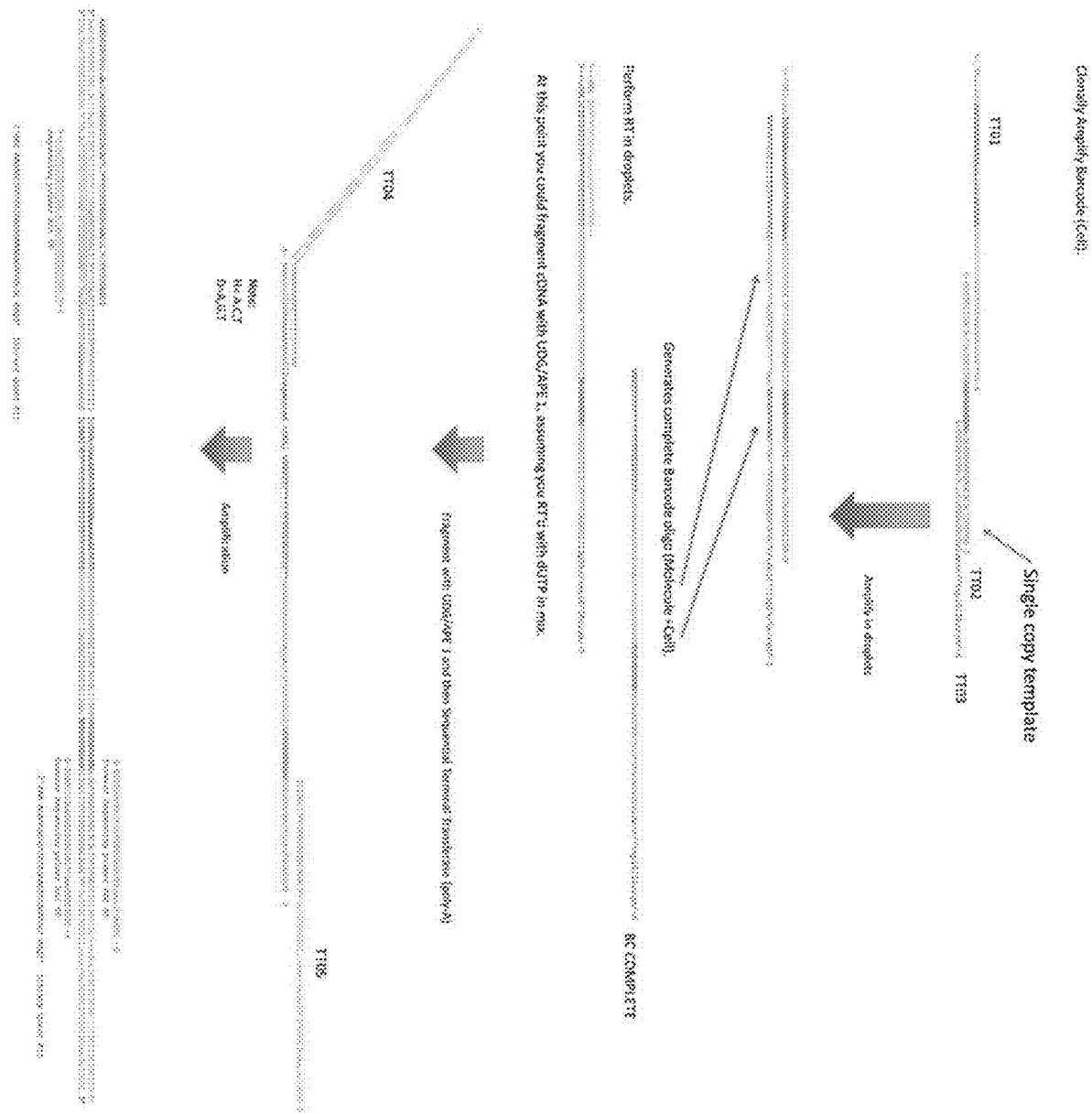
FIG. 6: Depicts a method for single cell messenger RNA analysis in droplets. Barcode oligonucleotides having a partition-specific and a molecular barcode are generated (SEQ ID NOS:13-29). Uracil (U) is incorporated in the place of thymine (T) at a defined U/T ratio into the reverse transcribed cDNA. Uracil DNA glycosylase/Apurinic endonuclease (UDG/ApeI) is used to fragment the cDNA. Terminal transferase adds multiple copies of a single polynucleotide to the fragments. Flanking primers TT04(SEQ ID NO:19) and TT05 (SEQ ID NOS:20-21) are used to incorporate adaptor sequences for high throughput sequencing.

A schematic of this example is depicted in FIG. 6. In a first step, droplets containing a linear polyacrylamide oligonucleotide conjugate (TT03); a bifunctional barcode nucleic acid template having a forward primer binding site, a reverse primer binding site, and a partition-specific barcode; and a biotin labeled reverse primer having a molecular barcode, a capture region, and a forward primer region are amplified by binding and polymerization of the forward and reverse primer in the droplets to generate a complete barcoded oligonucleotide conjugated to a bead (e.g., a hydrogel bead). In a second step, the biotinylated strand of the barcoded oligonucleotide is purified away. In a third step, the barcoded oligonucleotide conjugated beads, each bead having a unique particle barcode, are incorporated into droplets to obtain a population of droplets having an average of about 1 bead per droplet or less. The beads are used to prime reverse transcription of cellular RNA. Uracil is incorporated into the reverse transcribed cDNA. Uracil DNA glycosylase/ Apurinic endonuclease (UDG/ApeI) is used to fragment the cDNA. Terminal transferase adds multiple copies of a single poly-nucleotide to the fragments. Flanking primers TT04 and TT05 are used to incorporate adaptor sequences for high throughput sequencing.

Example 5

Synthesis of Barcoded Beads Using Reverse Amidites

Primer support 200 amino oligonucleotide synthesis resin is obtained from the manufacturer (GE Life Sciences). The amino resin is activated with 6-hydroxy hexanoic acid, remaining free amines are capped by acetylation with acetic anhydride. The synthesis procedure follows standard solid-phase phosphoramidite synthesis (e.g., as depicted at www.atdbio.com/content/17/Solid-phase-oligonucleotide-synthesis). However, the first coupling step uses a disulfide linker (e.g., www.glenresearch.com/ProductFiles/10-1936.HTML). Also, reverse amidites are used so the synthesis proceeds from 5'-3', which provides a 3'-OH free to initiate primer extension. During the synthesis, 8-15 contiguous bases are conjugated to the growing olignucleotide using the split-pool (split-and-mix) synthesis to provide a bead/cell barcode. In some cases, 4, 5, 6, 7, 8, 9, 10, 11, 12, or more contiguous bases are conjugated to the growing oligonucleotide as an equimolar or equikinetic mixture to provide a molecular barcode.

Example 6

Figure 7:
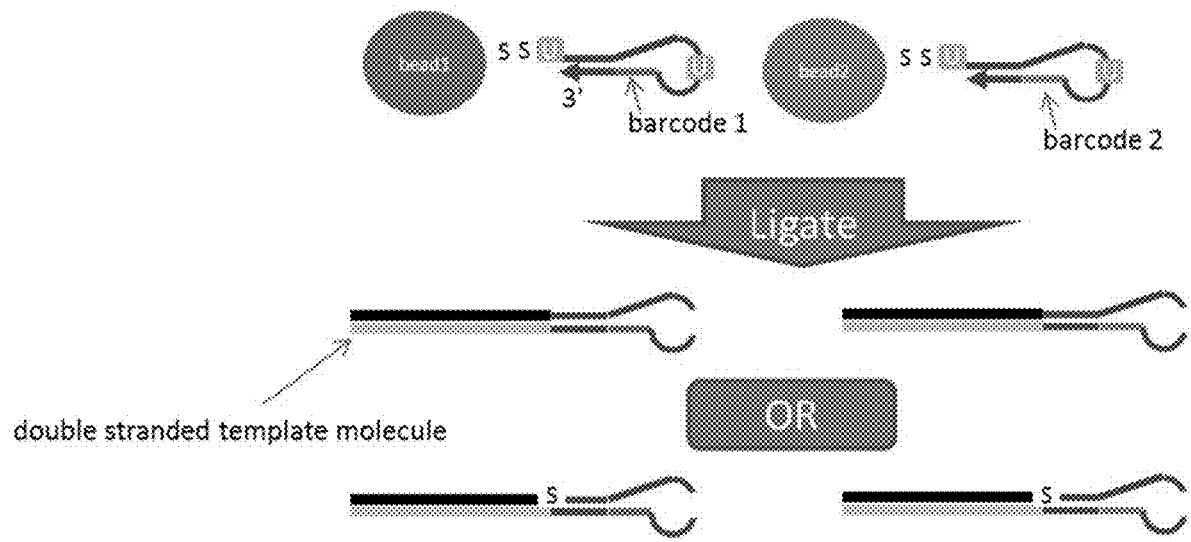
FIG. 7: Depicts a method for barcoding a nucleic acid by ligation. Hairpin barcoded oligonucleotides are synthesized onto a solid support (e.g., a bead) such that the oligonucleotides comprise a free 3' end for subsequent polymerization and/or ligation (e.g., using reverse phosphoramidite synthesis). Only two solid support immobilized barcoded hairpin oligonucleotides are shown. The oligonucleotides can be linked to the solid support by a disulfide linkage. A uracil can be used within the 5' end region (e.g., as the first base) of the oligonucleotide sequence. In some cases, 5' end region uracil is a 5' thiol modified uracil (e.g., 5'-thiol (thiohexyl; C6 modified). A uracil can also be incorporated into the hairpin region. The solid supports containing the hairpin barcoded oligonucleotides can be partitioned (e.g., partitioned into partitions containing a target nucleic acid or a target cell). In the partitions, the disulfide linkage can be cleaved if present to release oligonucleotides from the solid support. Similarly, uracil excision can be performed to release oligonucleotides, cleave the hairpin region, and/or provide a free 5' end for ligation to double stranded target nucleic acid (e.g., genomic fragments, cDNA, etc.). The cleaved and/or excised hairpin barcoded oligonucleotides can then be ligated to the double stranded target nucleic acid. In some cases, the 5' end sulfide of the oligonucleotides is not removed prior to ligation by, e.g., excision of a proximal uracil, resulting in a nicked DNA product (bottom).

Ligation of Barcoded Adaptors to Double Stranded Target Template Nucleic Acid Hairpin barcoded oligonucleotides are synthesized onto DNA synthesis resin using reverse phosphoramidite synthesis, which provides an oligonucleotide having a free 3' end. The oligonucleotides are linked to the solid support by a disulfide linkage. A 5'-thiohexyl modified uracil is used as 5' most base of the oligonucleotide sequence. A uracil is also incorporated into the hairpin region. The barcode is synthesized using a mix and split approach to produce bead/particle/cell barcodes. Alternatively, or in addition, a barcode is synthesized by sequential 3' addition of an equimolar or equikinetic mixture of nucleotides to produce a molecular barcode. The beads containing the hairpin barcoded oligonucleotides are partitioned. In the partitions, the disulfide linkage is cleaved to release oligonucleotides from the bead. Uracil excision is performed with UDG/ApeI to cleave, and thus linearize, the hairpin region and also provide a free 5' end for ligation to double stranded target nucleic acid (e.g., genomic fragments, cDNA, etc.). The cleaved and excised hairpin barcoded oligonucleotides are ligated to the double stranded target nucleic acid. Alternatively, the 5' end sulfide of the oligonucleotides is not removed prior to ligation by excision of the 5'-most uracil base, resulting in a nicked DNA product (FIG. 7, bottom).

Example 7

Figure 8:
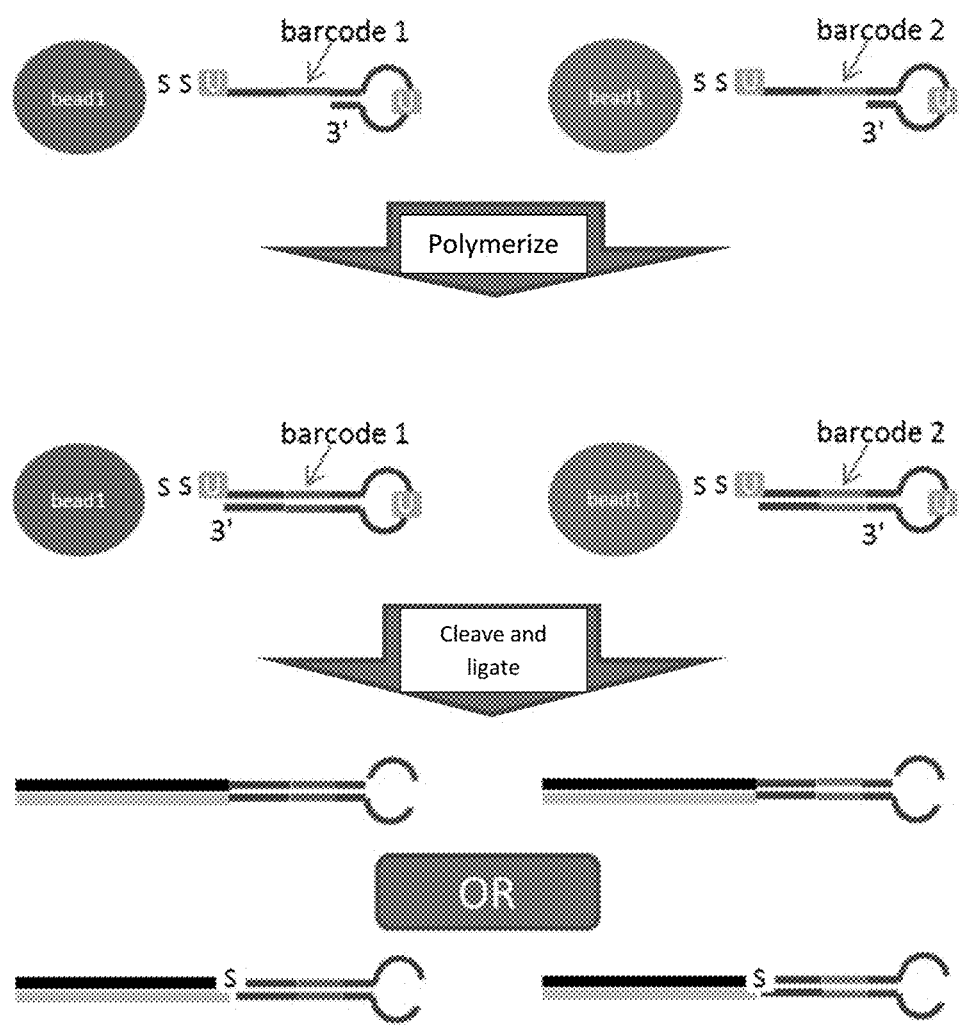
FIG. 8: Depicts a method for barcoding a nucleic acid by ligation. Hairpin barcoded oligonucleotides are synthesized onto a solid support (e.g., a bead) such that the oligonucleotides comprise a free 3' end for subsequent polymerization and/or ligation (e.g., using reverse phosphoramidite synthesis). Only two solid support immobilized barcoded hairpin oligonucleotides are shown. The oligonucleotides can be linked to the solid support by a disulfide linkage. A uracil can be used within the 5' end region (e.g., as the first base) of the oligonucleotide sequence. In some cases, 5' end region uracil is a 5' thiol modified uracil (e.g., 5'-thiol (thiohexyl; C6 modified). A uracil can also be incorporated into the hairpin region. DNA polymerase can be contacted with the solid support-bound oligonucleotides to extend the 3' end of the hairpin oligonucleotide and copy the barcode sequence. The solid supports containing the hairpin barcoded oligonucleotides can be partitioned (e.g., partitioned into partitions containing a target nucleic acid or a target cell). The partitioning can be performed before or after contacting with DNA polymerase to extend the 3' end of the hairpin oligonucleotides. In the partitions, the disulfide linkage can be cleaved if present to release oligonucleotides from the solid support. Similarly, uracil excision can be performed to release oligonucleotides, cleave the hairpin region, and/or provide a free 5' end for ligation to double stranded target nucleic acid (e.g., genomic fragments, cDNA, etc.). The cleaved and/or excised hairpin barcoded oligonucleotides can then be ligated to the double stranded target nucleic acid. In some cases, the 5' end sulfide of the oligonucleotides is not removed prior to ligation by, e.g., excision of a proximal uracil, resulting in a nicked DNA product (bottom).

Ligation of Barcoded Adaptors to Double Stranded Target Template Nucleic Acid Hairpin barcoded oligonucleotides are synthesized onto DNA synthesis resin using reverse phosphoramidite synthesis, which provides an oligonucleotide having a free 3' end. The oligonucleotides are linked to the solid support by a disulfide linkage. A 5'-thiohexyl modified uracil is used as 5' most base of the oligonucleotide sequence. A uracil is also incorporated into the hairpin region. The barcode is synthesized using a mix and split approach to produce bead/particle/cell barcodes. Alternatively, or in addition, a barcode is synthesized by sequential 3' addition of an equimolar or equikinetic mixture of nucleotides to produce a molecular barcode. DNA polymerase is contacted with the bead-bound oligonucleotides to extend the 3' end of the hairpin oligonucleotide and copy the barcode sequence. The beads containing the hairpin barcoded oligonucleotides are partitioned. The partitioning is performed before or after contacting with DNA polymerase to extend the 3' end of the hairpin oligonucleotides. The disulfide linkage is cleaved to release oligonucleotides from the solid support. Uracil excision is performed to release oligonucleotides, linearize the hairpin region, and also provide a free 5' end for ligation to double stranded target nucleic acid. The cleaved and excised hairpin barcoded oligonucleotides are ligated to the double stranded target nucleic acid. In some cases, the 5' end sulfide of the oligonucleotides is not removed prior to ligation by excision of the 5'-most uracil, resulting in a nicked DNA product (FIG. 8, bottom).

Example 8

Figure 9:
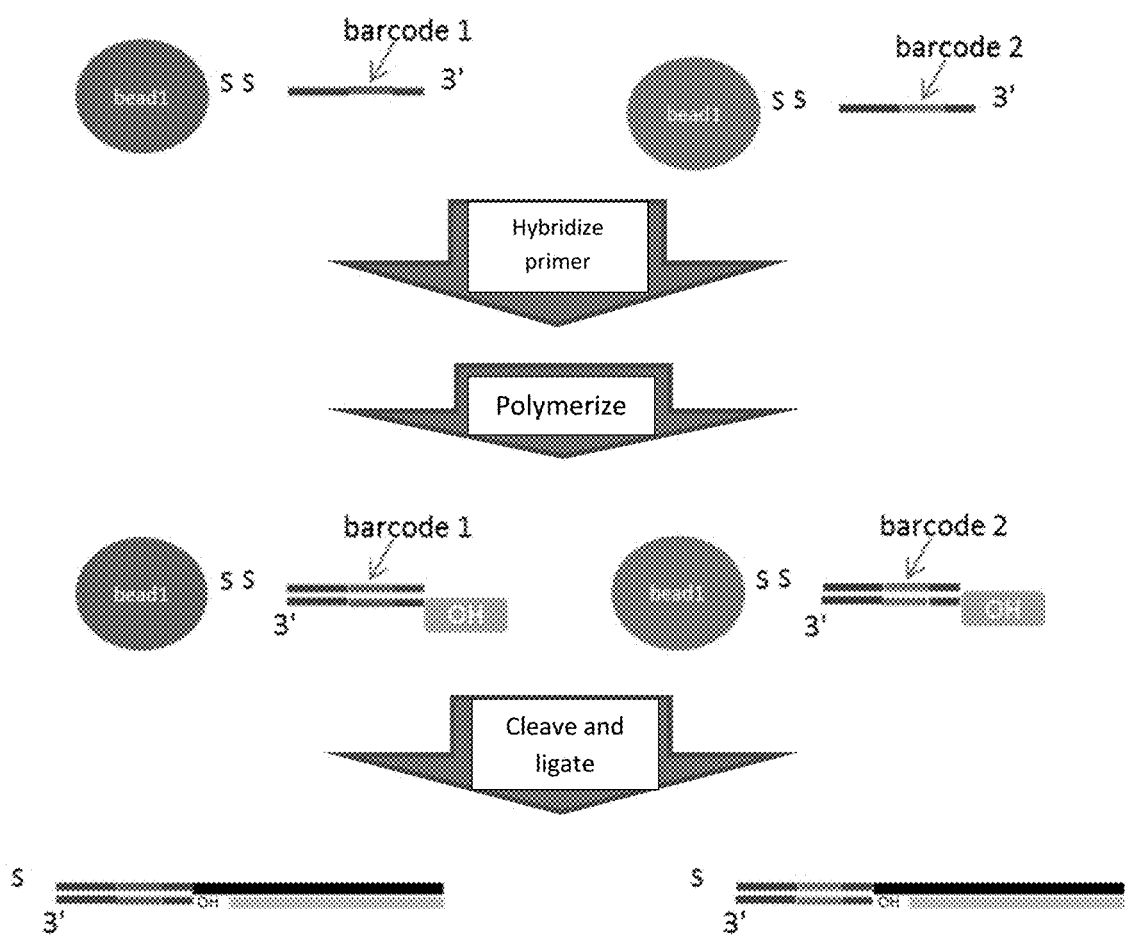
FIG. 9: Depicts a method for barcoding a nucleic acid by ligation. Barcoded oligonucleotides are synthesized onto a solid support (e.g., a bead) such that the oligonucleotides comprise a free 3' end for subsequent polymerization and/or ligation (e.g., using reverse phosphoramidite synthesis). Only two solid support immobilized barcoded oligonucleotides are shown. The oligonucleotides can be linked to the solid support by a disulfide linkage. A primer can be hybridized to the 3' end of the barcode oligonucleotides. DNA polymerase can be contacted with the oligonucleotides to produce a double stranded product. The primer can be passivated at the 5' end (e.g., with an OH group) so that only the top strand of the double stranded product is ligatable. The solid support immobilized stranded barcoded oligonucleotides can be partitioned (e.g., partitioned into partitions containing a target nucleic acid or a target cell). The partitioning can be performed before or after contacting with DNA polymerase to produce double stranded barcoded oligonucleotides. In the partitions, the disulfide linkage can be cleaved if present to release oligonucleotides from the solid support. The cleaved barcoded oligonucleotides can then be ligated to the double stranded target nucleic acid. Oligonucleotide ends with 5' OH termini are ligatable via the 3' end only.

Ligation of Barcoded Adaptors to Double Stranded Target Template Nucleic Acid The following Example is outlined in FIG. 9: Barcoded oligonucleotides are synthesized onto a DNA synthesis resin such that the oligonucleotides comprise a free 3' end for subsequent polymerization and/or ligation using reverse phosphoramidite synthesis. The oligonucleotides are linked to the solid support by a disulfide linkage. A primer is hybridized to the 3' end of the barcode oligonucleotides. DNA polymerase is contacted with the oligonucleotides to produce a double stranded product. The primer is passivated at the 5' end so that only the top strand of the double stranded product is ligatable. The barcoded oligonucleotide beads are partitioned. The partitioning is performed before or after contacting with DNA polymerase to produce double stranded barcoded oligonucleotides. In the partitions, the disulfide linkage is cleaved to release oligonucleotides from the beads. The cleaved barcoded oligonucleotides are ligated to the double stranded target nucleic acid. Oligonucleotide ends with 5' OH termini are ligatable via the 3' end only.

Example 9

Figure 10:
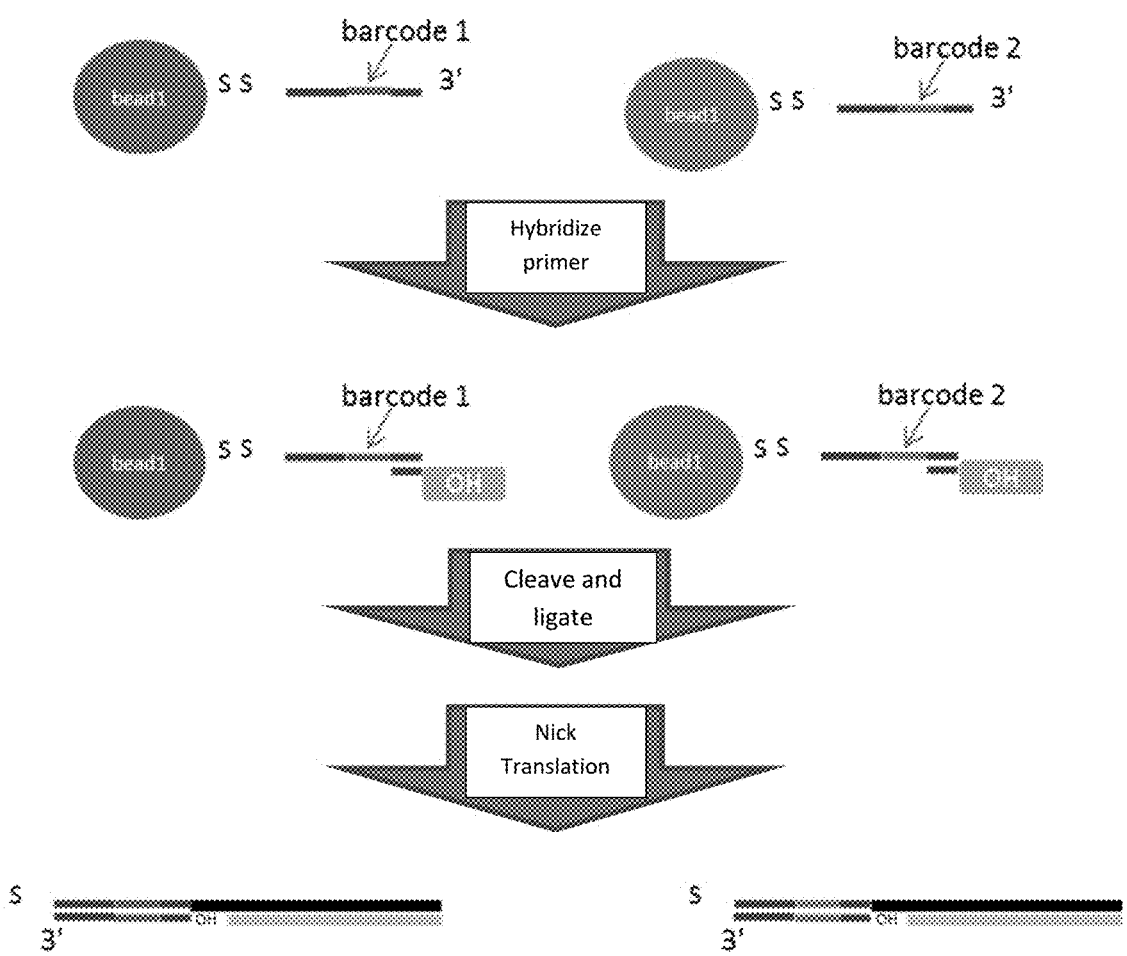
FIG. 10: Depicts a method for barcoding a nucleic acid by ligation. Barcoded oligonucleotides are synthesized onto a solid support (e.g., a bead) such that the oligonucleotides comprise a free 3' end for subsequent polymerization and/or ligation (e.g., using reverse phosphoramidite synthesis). Only two solid support immobilized barcoded oligonucleotides are shown. The oligonucleotides can be linked to the solid support by a disulfide linkage. A primer can be hybridized to the 3' end of the barcode oligonucleotides. The primer can be passivated at the 5' end (e.g., with an OH group) so that the 5' end of the primer cannot be ligated. The solid support immobilized stranded barcoded oligonucleotides can be partitioned (e.g., partitioned into partitions containing a target nucleic acid or a target cell). The partitioning can be performed before or after hybridization of the primer. In the partitions, the disulfide linkage can be cleaved if present to release oligonucleotides from the solid support. The cleaved barcoded oligonucleotides can then be ligated to the double stranded target nucleic acid. Oligonucleotide ends with 5' OH termini are ligatable via the 3' end only. Nick translation DNA synthesis can then be performed to copy the bottom strand of the adapter including the particle barcode sequence and the universal adapter sequence. Nick translation can be performed in the partitions, or after combining partitions.

Ligation of Barcoded Adaptors to Double Stranded Target Template Nucleic Acid The following Example is outlined in FIG. 10: Barcoded oligonucleotides are synthesized onto a DNA synthesis resin such that the oligonucleotides comprise a free 3' end for subsequent polymerization and/or ligation using reverse phosphoramidite synthesis. The oligonucleotides are linked to the solid support by a disulfide linkage. A primer is hybridized to the 3' end of the barcode oligonucleotides. The primer is passivated at the 5' end (e.g., with an OH group) so that the 5' end of the primer cannot be ligated. The barcoded oligonucleotide beads are partitioned. The partitioning is performed before or after hybridization of the primer. In the partitions, the disulfide linkage is cleaved to release oligonucleotides from the beads. The cleaved barcoded oligonucleotides are ligated to the double stranded target nucleic acid. Oligonucleotide ends with 5' OH termini are ligatable via the 3' end only. Nick translation DNA synthesis is performed to copy the bottom strand of the adapter including the particle barcode sequence and the universal adapter sequence. Nick translation is performed in the partitions, or after combining partitions.

Example 10

Single-Cell Targeted RNA-Seq

Figure 11:
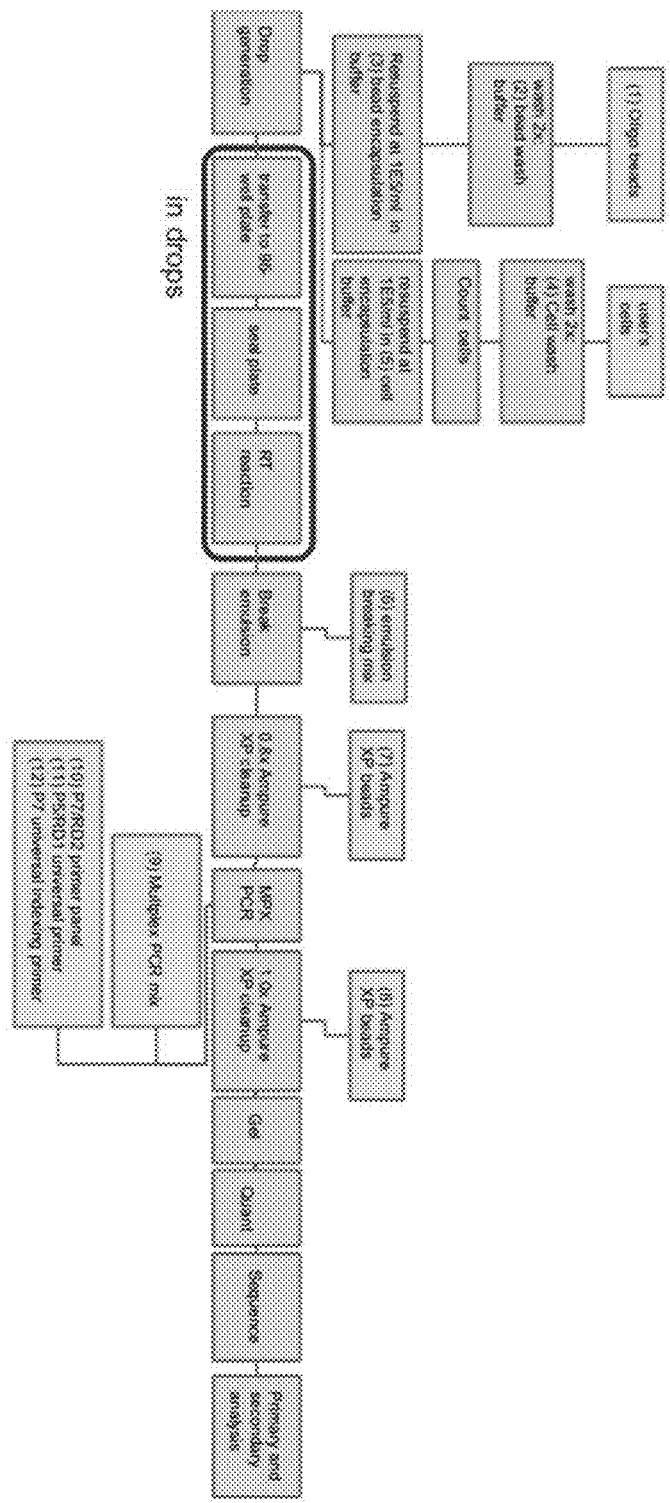
FIG. 11: Depicts a workflow for partitioning barcoded oligonucleotide beads into a plurality of single cell partitions for single cell RNA-seq.

Reagents: (numbers in parentheses refer to numbered boxes in FIG. 11)
(1) Barcoded oligonucleotide beads (Oligo beads). Stored in a buffer, such as TE to maintain stability of the DNA, and some sort of surfactant to prevent bead aggregation: pluronic F-68, F-98, tween-20, etc.
(2) Bead wash buffer: similar to bead storage buffer
(3) Bead encapsulation buffer: At least some of components necessary for RT reaction (Tris, magnesium, dNTPs, NaCl, or KCl, RT enzyme: the components are distributed across (3) and (5) such that RT cannot begin until both solutions are mixed at partition formation). Can contain components to buoyancy match beads: examples are optiprep, nycodenz (molecular density gradient media), Percoll or Ludox are silica nanoparticle-based density matching. Can also rely on polymers such as xanthan gum or ficoll, which increase viscosity in addition to a small amount of buoyancy matching. Buoyancy matching reduces the need to agitate the sample during encapsulation. The bead encapsulation buffer can also have a cell lysis reagent, such as a detergent, in it. Appropriate detergents that are known cell lysants and compatible with RT are non-ionics, such as Triton X-100, Brij-35, NP-40, Igepal-650.

(4) Cell wash buffer: Typically a pH-buffered, isotonic solution like PBS.

(5) Cell encapsulation buffer: At least some of components necessary for RT reaction (Tris, magnesium, dNTPs, NaCl, or KCl, RT enzyme: the components are distributed across (3) and (5) such that RT cannot begin until both solutions are mixed at drop formation) can include buoyancy matching reagent(s) as in (3). Can also contain reagent necessary for cleaving oligonucleotides off of the beads, such as TCEP or DTT. Typical concentrations are 2-4 mM TCEP and 10-50 mM DTT.

(6) Emulsion breaking mix is a compound to coalesce the droplet partitions. Suitable compounds are 2,2,3,3,4,4, 4-Heptafluoro-1-butanol, 1H,1H,2H,2H-Perfluoro-1-octanol, or chloroform.

(7) Ampure XP as bought from the manufacturer (8) Ampure XP as bought from the manufacturer (9) Multiplex PCR using a commercial multiplex mix.

Obtain cells from culture or disaggregated tissue. Wash 1-3 times in cell wash buffer, e.g., 1×PBS plus 0.01% pluronic F-68 by centrifuging for 1 min at 600×g and aspirating wash buffer. Count cells on a hemacytometer or automated cell counter. Resuspend in cell encapsulation buffer at $1 \times 10^5$ cells per ml. A suitable cell encapsulation buffer is 50 mM Tris pH8, dNTPs, RT enzyme, 4 mM TCEP, 5% optiprep and RNAse inhibitor. Wash beads 3 times in Bead wash buffer, e.g., TE+0.01% pluronic F-98. Resuspend at $1 \times 10^5$ beads per ml in bead encapsulation buffer, e.g., 1x RT buffer-dNTPs and enzyme, 50% optiprep, 0.1% Brij-35. Pipette 15 µl of bead suspension into each bead well of the microfluidic chip and 15 µl of cell suspension into each cell well. Pipette surfactant and oil into oil well. Place in a cell droplet generator instrument and activate droplet formation.

After drop formation, pipette drops and oil out of the sample wells and into a 96-well plate. Place in the block of a thermal cycler and incubate at 50° C. for 1-2 hours for reverse transcription and cell lysis followed by 85° C. for 10-20 minutes to denature the reverse transcriptase enzyme.

To break the emulsion, pipette samples from the plate and combine like samples into a single 1.5 ml centrifuge tube. Centrifuge for 1 min at 1000×G and remove bottom oil layer. Add breaking solution, e.g., 20% 2,2,3,3,4,4,4-Heptafluoro-1-butanol in HFE7500, vortex and centrifuge again. Remove the clear aqueous phase from the top and proceed with library construction and high throughput sequencing.

Example 11

Figure 12:
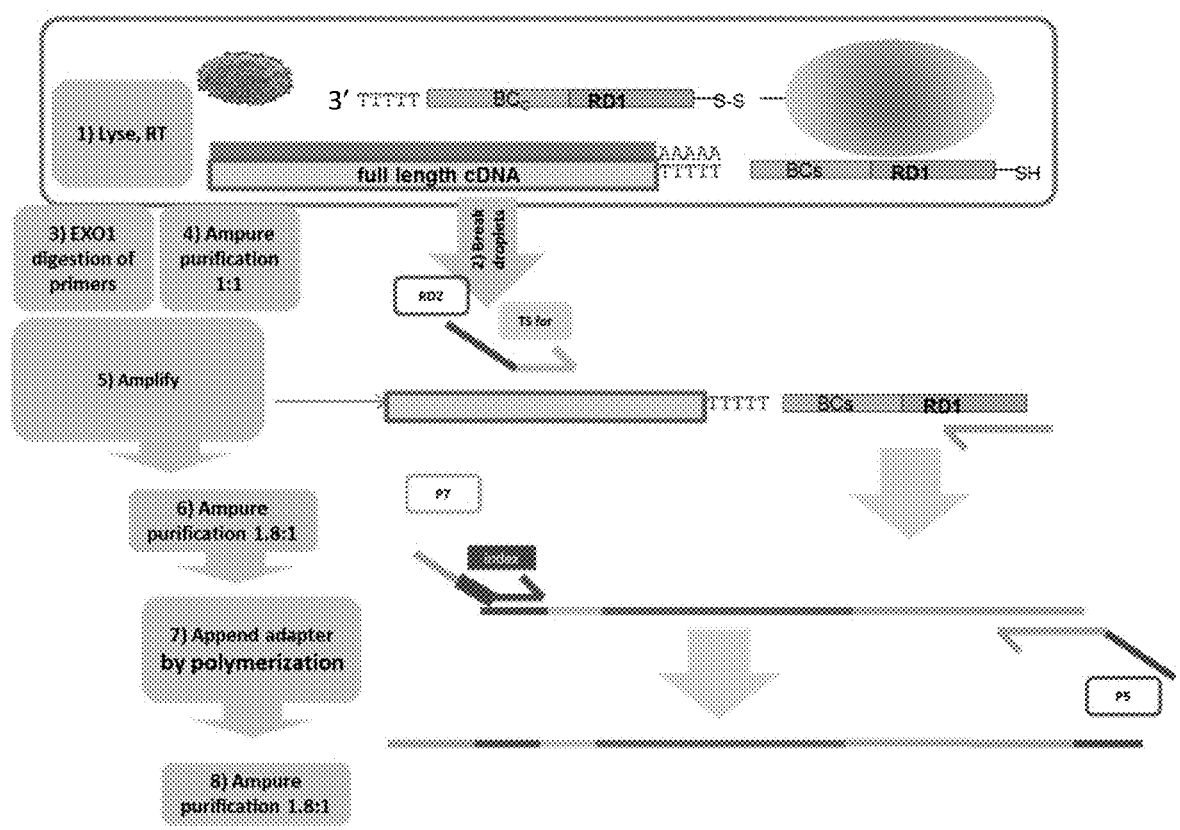
FIG. 12: Depicts a schematic for a method of using of barcoded oligonucleotide beads for high throughput cDNA sequencing. In this schematic, barcode (BC) oligos having a particle and a molecular barcode are generated on solid support particles. The oligonucleotides can be linked to the solid support by a disulfide linkage. The oligonucleotides can comprise a free 3' end for subsequent hybridization and polymerization or conversion to a ligatable (e.g., double stranded) end. The oligonucleotides can have a poly-thymine region comprising from about 15 to about 20, or from about 15 to about 35, thymine nucleotides for mRNA capture. The oligonucleotides can have 5' positioned universal tags. 5' universal tags can include a RD1 sequence from the P5 adapter (Illumina), or a sequence complementary to the RD1 sequence. In partitions, a sample containing nucleic acids can be partitioned together with the oligonucleotide barcoded beads. The sample may include cells. In some cases, the sample and oligonucleotide barcoded beads is partitioned such that, on average, the partitions contain no more than 1 bead and/or cell. In the partitions, cells can be lysed. In the partitions, oligonucleotides can be released from the beads. Oligonucleotide release can be achieved with a reducing agent where disulfide bonds link the oligonucleotide to the solid support. Hybridization of oligonucleotides to nucleic acid targets occurs and the substrate is polymerized. The target nucleic acid can be RNA. Polymerization can be reverse transcription. Partitions can be combined. If partitions are droplets, the emulsification can be broken by use of a detergent. Alternatively, after hybridization of oligonucleotides to nucleic acid targets, partitions are combined and polymerization occurs in bulk reactions. Exonuclease I can be used to digest unbound primer. Products can be purified, e.g., with Ampure bead purification. Target nucleic acids are amplified using oligonucleotides that are complementary to target sequences in the substrate and to the universal portion of the barcode oligonucleotide. The oligonucleotides may be tailed with further universal primer sequences. Products can be purified, e.g., with Ampure bead purification. Further amplification may be performed with oligonucleotides that hybridize to the products from the first amplification reaction. The oligonucleotides may be tailed with further universal primer sequences and with indexes used in next generation sequencing. Products may be further purified, e.g., with Ampure bead purification.

Barcoding and Amplification of Target Nucleic Acid Using a Molecular Barcoded Bead The following Example is outlined in FIG. 12: (1) cells are partitioned with reverse amidite synthesized oligonucleotide beads having a 3' end free for polymerization. The effect of the presence or absence of a 10 nucleotide molecular barcode sequence on oligonucleotide beads is tested in parallel experiments. Cells are partitioned with molecular barcoded or non-barcoded beads. The oligonucleotides contain from 3' to 5': a poly-thymine sequence at the 3' end, an optional molecular barcode, a disulfide linkage to a bead at the 5' end. Cells are lysed, the oligonucleotides are released from the beads with a reducing agent, poly-adenylated mRNA is hybridized to the poly-thymine region of the oligonucleotides, and reverse transcription is performed. (2) Droplets are combined and (3) primers are removed by ExoI digestion. (4) The resulting product is purified with Ampure XP beads. Adaptors for high throughput sequences are appended via two-step amplification as follows: (5) RD2 and RD1 primers are appended in a first amplification; (6) the product is purified using ampure beads; and, (7) P7 and P5 are appended in a second amplification. Two different commercially available amplification mixes are tested for step (5). One step amplification for appending P7 and P5 adaptors is also tested (not depicted).

The resulting amplification products are tested for DNA fragment size distribution by experion gel electrophoresis. The results show that the expected size of 250-750 bp fragments are obtained whether or not molecular barcodes are present, whether or not high throughput sequencing adaptors are added in a one-step, or two-step amplification, and regardless of the amplification mix used in step (5). One-step amplification is slightly less efficient, likely due to the use of a lower primer concentration. Non-templated amplification is minimal or absent in the samples. The resulting amplification products were further tested for NTC qPCR contributions to sample data by melting curve analysis. The delta Ct is 6 or greater for the tested samples. Thus the contribution to Sample Ct is ~1% or less. Thus, there are no significant NTC qPCR contributions to sample data. qPCR analysis of amplification products showed that the one-step amplification method does not produce significant library bias. Target enrichment (or loss) was measured by detecting GAPDH copy number via ddPCR. Approximately 8000 fold enrichment was achieved using one-step amplification with Bio-Rad Preamp Supermix in step (5) and a molecular barcoded bead.

What is claimed is:

1. A method of analyzing the nucleic acid of a plurality of cells comprising:

forming a plurality of partitions, wherein each partition comprises:

a particle comprising a population of oligonucleotides having a single-stranded barcode unique for that particle and a capture sequence, wherein the oligonucleotides comprise a 5' thiol modified uracil that is linked via a disulfide linkage to the particle and a 3' end that is available for extension by a polymerase, and wherein the oligonucleotides comprise a hairpin that includes a uracil and wherein the particle is a hydrogel; and a sample comprising a double-stranded target nucleic acid;

cleaving the disulfide linkage to release the oligonucleotides and to form a released 5' end;

extending the 3' end with a polymerase;

performing uracil excision to cleave the oligonucleotides at the hairpin thereby forming double-stranded oligonucleotides;

after the performing, ligating the 3' end and optionally the released 5' end of the double-stranded oligonucleotides to at least a portion of the target nucleic acid in each partition, thereby covalently attaching the double-stranded oligonucleotides to at least a portion of the target nucleic acid in each partition, wherein the ligating is performed before combining partitions;

combining the partitions; and performing high throughput sequencing.

2. The method of claim 1, wherein the sample comprising target nucleic acid comprises a cell containing the target nucleic acid.

3. The method of claim 2, wherein prior to the ligating, the cell is lysed.

4. The method of claim 1, wherein the sample comprising target nucleic acid comprises DNA.

5. The method of claim 1, wherein the sample comprising target nucleic acid comprises long fragment DNA.

6. The method of claim 4, wherein the DNA is double stranded.

7. The method of claim 1, wherein the providing comprises
   (a). conjugating a reverse amidite nucleotide to a plurality of precursor particles, wherein the conjugating is performed in at least four separate reactions, each reaction conjugating a different reverse amidite nucleotide, and wherein after the conjugating, the particles are combined and mixed;
   (b). repeating (a) from 6-20 times, thereby generating a plurality of barcoded particles, wherein the individual barcoded particles comprise oligonucleotides comprising a plurality of copies of a particle-specific barcode, wherein the individual oligonucleotides comprise a 5' and a 3' end, the oligonucleotides are conjugated to the particles at the 5' end, and the 3' end is available for ligation and/or extension by a polymerase; and
   (c). partitioning the barcoded particles, thereby generating a plurality of partition-specific barcoded partitions.

8. The method of claim 1, wherein partitions contain a single cell or nucleic acid from a single cell.

9. The method of claim 1, wherein the partitions are droplets surrounded by an immiscible liquid.

10. The method of claim 9, wherein the providing comprises forming the droplets in a microfluidic device.

11. The method of claim 1, further comprising deconvoluting the barcodes after the high throughput sequencing to associate the barcodes with cells or nucleic acids.

12. The method of claim 1, wherein the forming comprises merging a stream of the particles with a stream of cells to form droplets comprising a cell and a particle.

13. The method of claim 12, wherein the stream of particles comprises a cell lysis reagent that lysis cells in the droplets following the merging.

14. The method of claim 13, wherein the cell lysis reagent is a detergent.

15. The method of claim 1, wherein the forming comprises:
   providing a mixture of droplets, wherein individual droplets comprise a cell and a particle; and
   heating the droplets.

16. The method of claim 1, wherein the extending forms a complementary sequence of the barcode.

17. The method of claim 1, wherein the hairpin comprises the barcode.

18. The method of claim 1, wherein the released 5' end is ligated to the target nucleic acid.

* * * * *